United States Patent
Voldman et al.

(10) Patent No.: US 7,425,253 B2
(45) Date of Patent: Sep. 16, 2008

(54) MICROSCALE SORTING CYTOMETER

(75) Inventors: Joel Voldman, Somerville, MA (US); Brian Michael Taff, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 158 days.

(21) Appl. No.: 11/045,487

(22) Filed: Jan. 31, 2005

(65) Prior Publication Data

US 2005/0175981 A1 Aug. 11, 2005

Related U.S. Application Data

(60) Provisional application No. 60/539,567, filed on Jan. 29, 2004.

(51) Int. Cl.
*G01N 27/447* (2006.01)
*G01N 27/453* (2006.01)

(52) U.S. Cl. .................. 204/547; 204/643

(58) Field of Classification Search ............... 73/865.5; 422/73; 204/547, 643
See application file for complete search history.

(56) References Cited

U.S. PATENT DOCUMENTS

| | | | | |
|---|---|---|---|---|
| 4,661,451 A * | 4/1987 | Hansen | ........ | 435/174 |
| 6,448,794 B1 * | 9/2002 | Cheng et al. | ........ | 324/693 |
| 6,716,642 B1 * | 4/2004 | Wu et al. | ........ | 436/518 |
| 6,730,516 B2 * | 5/2004 | Jedrzejewski et al. | ........ | 436/43 |
| 6,838,056 B2 * | 1/2005 | Foster | ........ | 422/100 |
| 6,916,541 B2 * | 7/2005 | Pantano et al. | ........ | 428/429 |

OTHER PUBLICATIONS

Voldman et al. ("A Microfabricated-Based Dynamic Array Cytometer," Anal. Chem. 2002, 74, 3984-3990).*
Chaudhari, A. M., Woudenberg, T. M., Albin, M. & Goodson, K. E. Transient liquid crystal thermometry of microfabricated PCR vessel arrays. Journal of Microelectromechanical Systems 7, 345-355 (1998).
Fujii, G., Tsuchiya, R., Ezoe, E. & Hirohashi, S. Analysis of nuclear localization signals using a green fluorescent protein-fusion protein library. Exp Cell Res 251, 299-306. (1999).
Guet, C. C., Elowitz, M. B., Hsing, W. & Leibler, S. Combinatorial synthesis of genetic networks. Science 296, 1466-70. (2002).
Lippincott-Schwartz, J., Snapp, E. & Kenworthy, A. Studying protein dynamics in living cells. Nat Rev Mol Cell Biol 2, 444-56. (2001).
Peelle, B. et al. Intracellular protein scaffold-mediated display of random peptide libraries for phenotypic screens in mammalian cells. Chem Biol 8, 521-34. (2001.
Rolls, M. M. et al. A visual screen of a GFP-fusion library identifies a new type of nuclear envelope membrane protein. J Cell Biol 146, 29-44. (1999).

(Continued)

*Primary Examiner*—Alex Noguerola
(74) *Attorney, Agent, or Firm*—Pearl Cohen Zedek Latzer, LLP; Mark Cohen

(57) ABSTRACT

The present invention provides a device and methods of use thereof in microscale cell sorting. This invention provides sorting cytometers, which trap individual cells within vessels following exposure to dielectrophoresis, allow for the assaying of trapped cells, such that a population is identified whose isolation is desired, and their isolation.

24 Claims, 32 Drawing Sheets

OTHER PUBLICATIONS

Rutter, G. A., Kennedy, H. J., Wood, C. D., White, M. R. H. & Tavare, J. M. Real-time imaging of gene expression in single living cells. Chemistry & Biology 5, R285-R290 (1998).

Shioda, T., Andriole, S., Yahata, T. & Isselbacher, K. J. A green fluorescent protein-reporter mammalian two-hybrid system with extrachromosomal maintenance of a prey expression plasmid: application to interaction screening. Proc Natl Acad Sci U S A 97, 5220-4. (2000).

Taylor, D. L., Woo, E. S. & Giuliano, K. A. Real-time molecular and cellular analysis: the new frontier of drug discovery. Current Opinion in Biotechnology 12, 75-81 (2001).

Ting, A. Y., Kain, K. H., Klemke, R. L. & Tsien, R. Y. Genetically encoded fluorescent reporters of protein tyrosine kinase activities in living cells. Proc Natl Acad Sci U S A 98, 15003-8. (2001).

Tsien, R. Y. The green fluorescent protein. Annual Review of Biochemistry 67, 509-544 (1998).

Voldman, J., Braff, R. A., Toner, M., Gray, M. L. & Schmidt, M. A. Holding Forces of Single-Particle Dielectrophoretic Traps. Biophys. J. 80, 531-541 (2001).

Voldman, J., Toner, M., Gray, M. L. & Schmidt, M. A. A Microfabrication-Based Dynamic Array Cytometer. Analytical Chemistry 74, 3984-3990 (2002).

Zhang, J., Campbell, R. E., Ting, A. Y. & Tsien, R. Y. Creating new fluorescent probes for cell biology. Nat Rev Mol Cell Biol 3, 906-18 (2002).

Archer, et al (1999) "Cell Reactions to Dielectrophoretic Manipulation." Biuochemical and Biophysical Research Communications 257, 687-698.

Chiou, et al (2005) "Massively parallel manipulation of single cells and microparticles using optical images." Nature vol. 436 doc. 10.1038.

Fiedler, et al (1998) "Dielectrophoretic Sorting of Particles and Cells in a Microsystem." Anal. Chem. 70, 1909-1915.

Fuhr, et al (1994) "Cell manipulation and cultivation under a.c.electric field influence in highly conductive culture media." Biochimica et Biophysica Acta 1201 353-360.

Gray, et al (2004) "Dielectrophoretic Registration of Living Cells to a microelectrode array." Biosensors and Bioelectronics 19, 771-780.

Ramos, et al (1998) "An electrokinetics: A review in forces in microelectrode structures." J.Phys. D. Appl. Phys 31, 2338-2353.

Rosenthal, et al (2005) "Dielectrophoretic traps for single-particle patterning." Biophysical Journal vol. 88 2193-2205.

Rosenthal, et al (2006) "Quantitive modeling of Dielectrophoretic traps." Paper.

Taff, et al (2005) "A Scalable Addressable Positive-Dielectrophoretic Cell-Sorting Array." Anal. Chem. 77 7976-7983.

Zimmerman, et al (2000) "Electromanipulation of Mammalian Cells: Fundamentals and Application." IEEE Transactions on Plasma Science vol. 28 No. 1.

Grimm, et al (2004) The Art and Design of Genetic Screens:Mammilian Culture Cells. Nature Reviews: Genetics 5, 179-189.

Moffat, et al (2006) "Building Mammalian Signaling Pthways with RNAi Screens." Nature Reviews: Molecular Cell Biology 7, 177-187.

Kholodenko, et al (2006) "Cell Signaling Dynamics in Time and Space." Nature Reviews: Molecular Cell Biology 7, 165-175.

Kiger, et al (2003) "A Functional Genomic Analysis of Cell Morphology Using RNA Interference." Journal of Biology 2:27.

Manaresi, et al (2003) "A CMOS Chip for Individual Cell Manipulation and Detection." IEEE Journal of Solid State Circuts 38: 12 2297-2305.

Suehiro, et al (1998) "The Dielectrophoretic Movement and Positioning of a Biological Cell Using a Three Dimensional GridElectrode Syatem." Journal Phys. D: Appl. Phys. 31 3298-3305.

Perlman, et al (2004) "Drug profiling by Automated Microscopy." Science 306 1194-1198.

Glasser, et al (1998) "Cultivation of Cells under strong ac electric field differentiation between heating and trans-membrane potential effects." Bioelectrochemistry and Bioenergenics 47 301-310.

\* cited by examiner

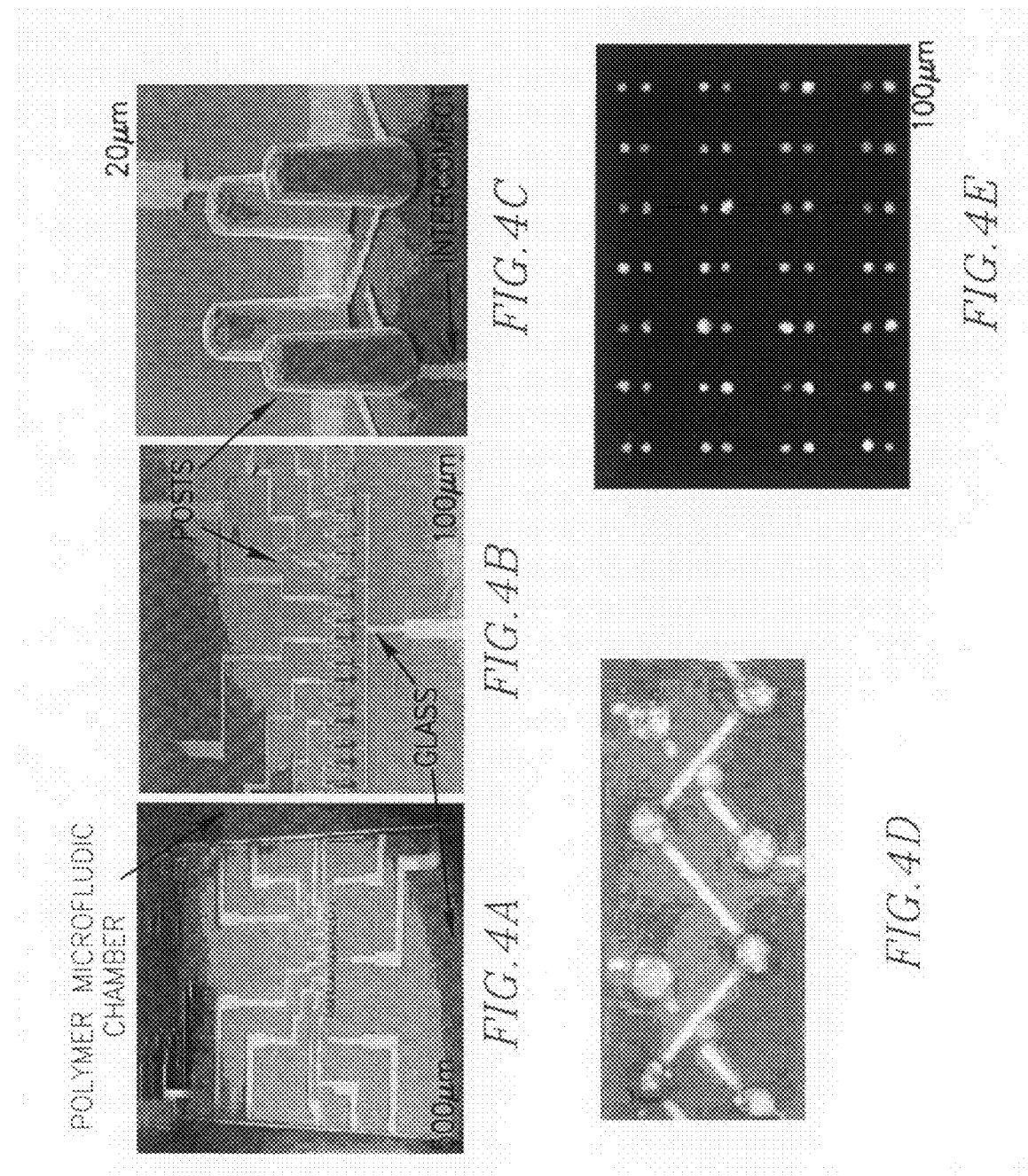

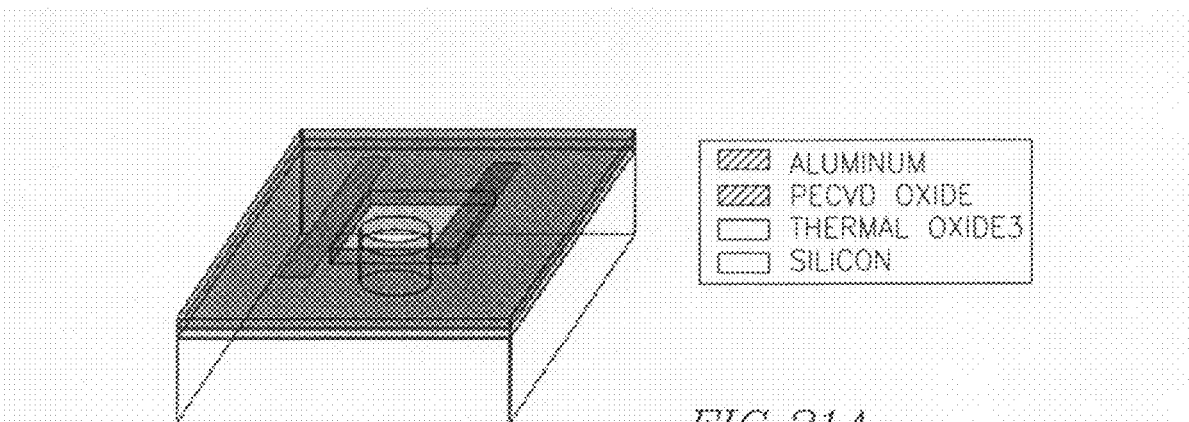
*FIG.21A*
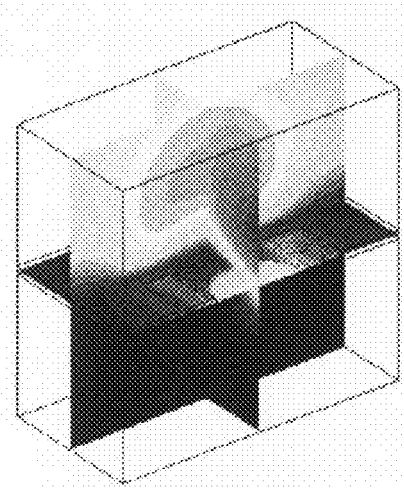
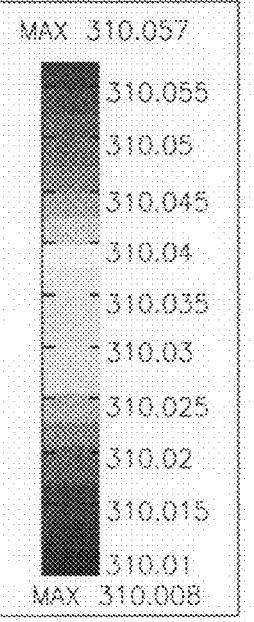
*FIG.21B*
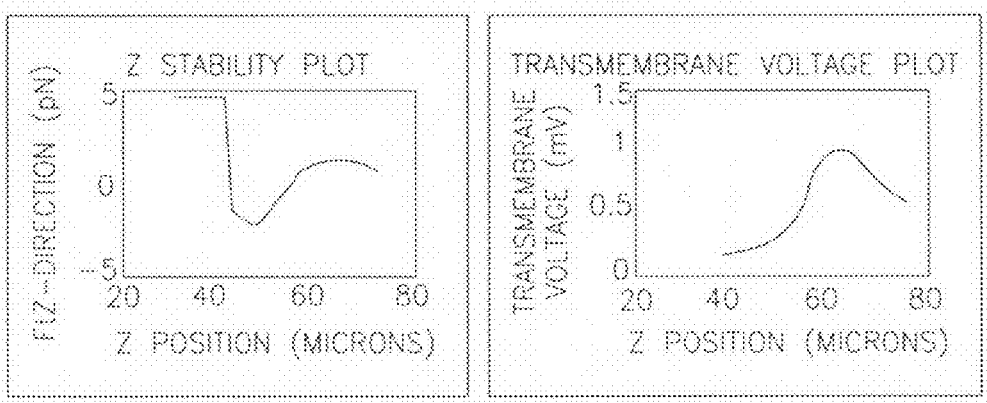
*FIG.21C*

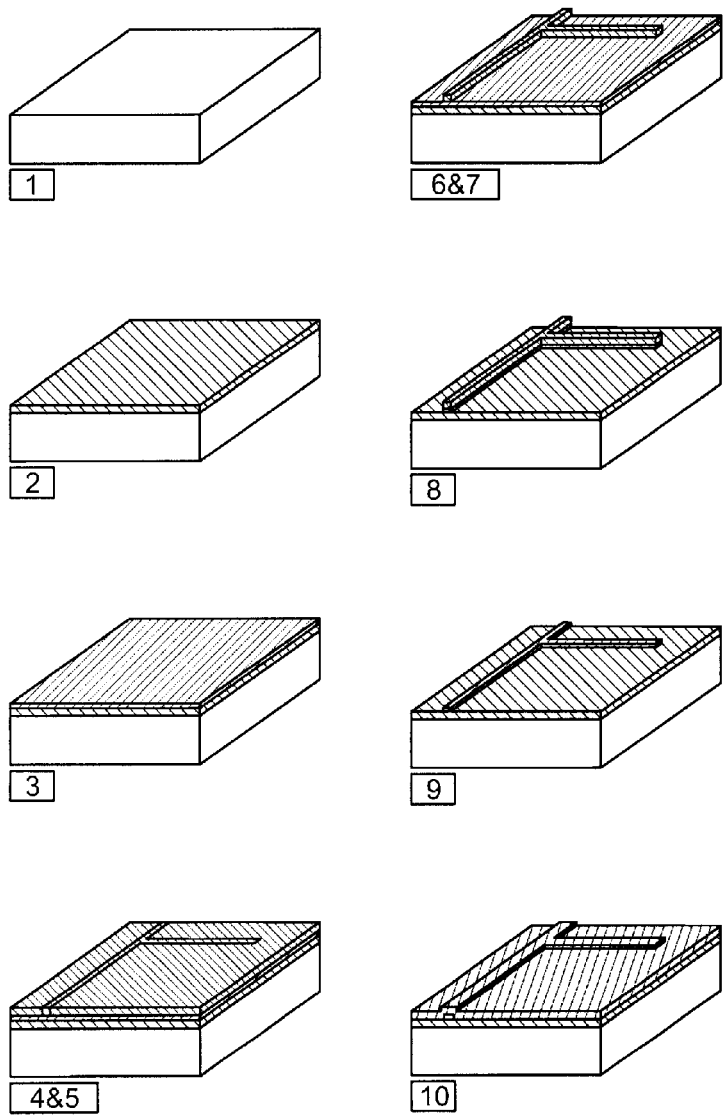
FIG. 24 (Contd.)

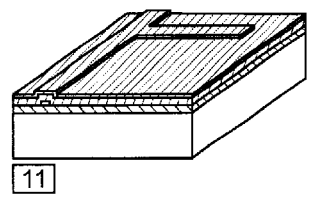
11
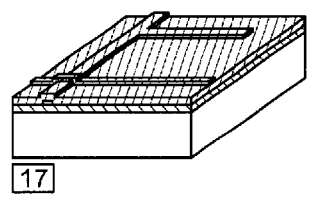
17
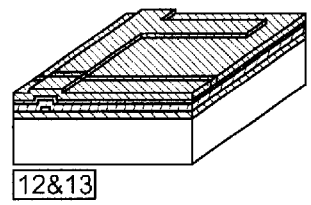
12&13
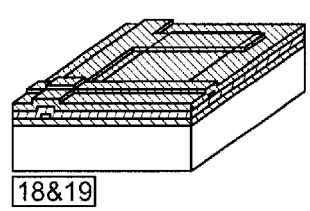
18&19
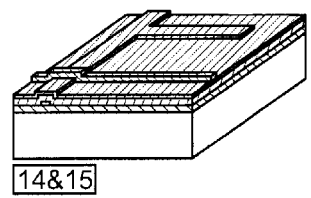
14&15
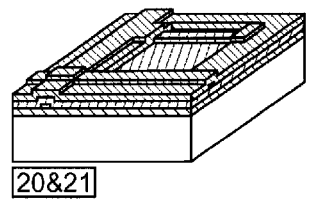
20&21
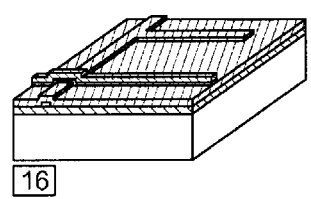
16
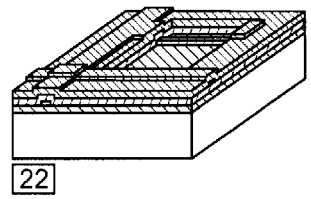
22
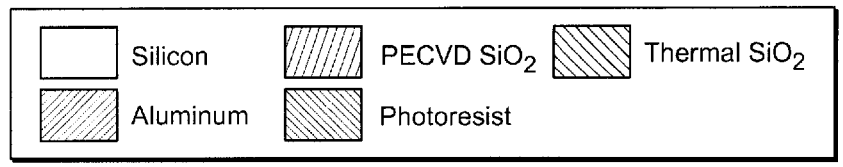
FIG. 24 (Contd.)

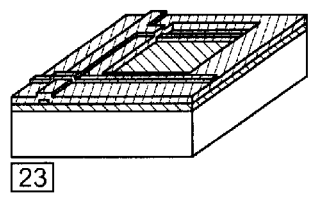
[23]
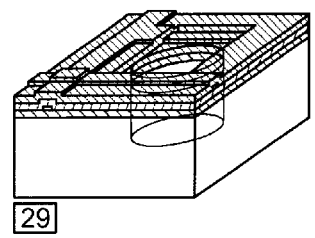
[29]
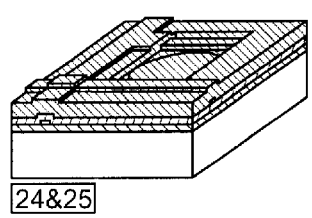
[24&25]
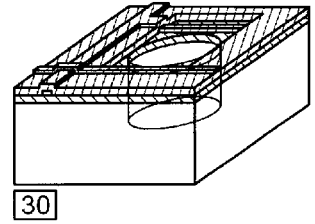
[30]
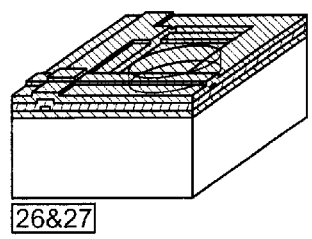
[26&27]
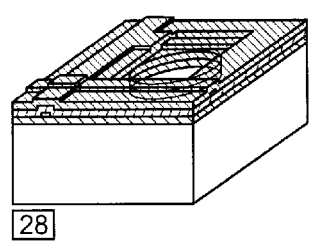
[28]
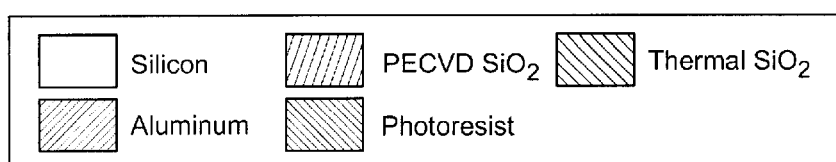
FIG. 24 (Contd.)

MICROSCALE SORTING CYTOMETER

CROSS-REFERENCE TO RELATED APPLICATIONS

This Application claims priority from U.S. Provisional Application Ser. No. 60/539,567, filed Jan. 29, 2004, which is hereby incorporated in its entirety.

FIELD OF THE INVENTION

This invention provides devices and methods of use thereof in cell sorting This invention provides a microscale sorting cytometer, which is based on the dielectrophoretic manipulation of individual cells, which can be analyzed and subsequently sorted.

BACKGROUND OF THE INVENTION

Systematic investigation and understanding of cells depends on the tools available with which to probe cell function. Although cells exhibit complex intracellular and morphological behavior, and carry out functions over time, limitations in the ability to genetically probe these processes directly hinders the ability to understand cell function. Currently, an ability to observe cells microscopically and then arbitrarily sort subpopulations of the observed cells, on a reasonably large scale, is lacking.

Flow cytometry and the related fluorescence-activated cell sorting (FACS) flow cells in a buffer single-file past an interrogation point, allowing high-throughput (>10,000 cells/sec) analysis of light scatter and whole-cell fluorescence, however, flow sorters do not image, making them unable to sort based upon morphological or intracellular information, and their very nature as flowing systems makes it difficult to observe the same cell at widely spaced timepoints, as would be needed to screen for temporal behavior. Attempts have been made to create flow cytometers that can obtain intracellular and dynamic information, such as slit-scan flow cytometers and imaging flow cytometry that can image micron-sized particles as they pass the observation point, however they cannot sort cells, and cannot assay cells adhered to substrates as is desirable for imaging and for investigating processes specific to adherent cells.

The complementary technology to flow cytometry is microscopy. In microscopy, cells are randomly arrayed on a coverslip or multi-well plate and then observed. Observation can include intracellular and/or temporal imaging. Many advanced microscopy technologies have been developed over the years to enhance screening capabilities. Today, all major microscopy manufacturers offer fluorescence microscopes with automated stages, focusing, objectives, fluorescence filters, etc. In conjunction with commercially available software (e.g., Metamorph by Universal Imaging), these allow computer-controlled location and observation of cells over time and space. In addition, specific high-throughput imaging systems have been optimized for pharmaceutical screening (e.g., Cellomics, Automated Cell Inc.). All conventional microscopy technologies, however, are limited in their ability to viably isolate cells following imaging.

Cell-based genetic screens, employing the observation of cells and their isolation when exhibiting a desired phenotype, has been accomplished via the use of microscopy, however, its use is severely limited in its ability to isolate positive-responding cells. The premiere isolation technique, fluorescence-activated cell sorting (FACS), another means of isolating cells with a desired phenotype is limited in terms of the phenotypic changes that can be observed. A gap therefore exists between what is observable micropcopically, and what may be isolated, with a clear and present need for a technology that effectively bridges the gap.

SUMMARY OF THE INVENTION

The invention provides, in one embodiment, a method for adherent cell sorting, comprising loading cells in a sorting cytometer, comprising:
  a. an array;
  b. a power source;
  c. an input port coupled to said array;
  d. vessels, with dimensions such that it holds a single cell;
  e. dielectrically separated crossing electrodes coupled to said power source, surrounding said vessels arranged in a row/column addressing scheme on said array; and
  f. an output port coupled to said array;

such that individual cells passively enter said vessel; applying a voltage, such that the individual cells are subjected to dielectrophoresis, and arc physically trapped within each vessel, under conditions allowing the trapped cells to adhere to the vessel; assaying adherent cells upon cessation of the application of voltage, such that a population of said adherent cells is identified whose isolation is desired; reapplying voltage to vessels comprising cells whose isolation is not desired, trapping these cells; dislodging cells whose isolation is desired, and collecting these cells from the output port.

In one embodiment, the dielectrophoresis is positive or negative. In another embodiment, the applied voltage is between 1 and 15 V. In another embodiment, the cytometer is maintained under controlled temperature, pH, $CO_2$ or Oxygen conditions, or a combination thereof. In another embodiment, the array is comprised of a transparent material. In another embodiment, the transparent material is pyrex, quartz or SU-8. In another embodiment, the array is comprised of a silicone. In another embodiment, the array is coated with a low-autofluorescent material. In another embodiment, the array, with the exception of the vessels, are coated with a microstamping material. In another embodiment, the microstamping material is polyethylene glycol or octadecyl-trichlorosilane. In another embodiment, the vessels are coated with a positively charged material. In another embodiment, the vessels are coated with at least one protein, which, in another embodiment, is an extracellular matrix protein.

In another embodiment, the cells comprise a vector, which, in another embodiment, comprises a reporter, which, in another embodiment, is fluorescent. In another embodiment, assaying the cells produces at least 2 distinguishable cell populations. In another embodiment, the population of adherent cells is identified by fluorescence microscopy. In another embodiment, dislodging the cells is effected by the introduction of a solution in said input port, which, in another embodiment, comprises trypsin, elastase, papain, a high salt concentration or a chelating agent, or a combination thereof. In another embodiment, the method is used for the identification of a diseased cell.

In another embodiment, this invention provides a sorting cytometer for eukaroytic and/or prokaryotic cells comprising an array; a power source; an input port coupled to the array; vessels, with dimensions such that it holds a single cell; dielectrically separated crossing electrodes coupled to the power source, surrounding the vessels, arranged in a row/column addressing scheme on the array; and an output port coupled to the array.

In another embodiment, dielectrically separated crossing electrodes on said array induce positive or negative dielectrophoresis of cells applied to said cytometer. In another embodiment, the voltage applied is between 1 and 15 V. In another embodiment, the cytometer is maintained under controlled temperature, pH, $CO_2$ or Oxygen conditions, or a combination thereof. In another embodiment, the array is comprised of a transparent material. In another embodiment, the transparent material is pyrex, quartz or SU-8. In another embodiment, the array is coated with a low-autofluorescent material. In another embodiment, the array, with the exception of said vessels, is coated with a microstamping material, which, in another embodiment is polyethylene glycol or octadecyl-trichlorosilane. In another embodiment, the vessels are coated with a positively charged material. In another embodiment, the vessels are coated with at least one protein, which, in another embodiment, is an extracellular matrix protein.

In another embodiment, an illumination source is operatively positioned to direct radiation to said vessels, which is one embodiment is a laser. In another embodiment, a beam splitter is employed with the use of said illumination source. In another embodiment, a recording device is operatively positioned to record a parameter in said cytometer. In another embodiment, the recording device is a camera, a computer, a luminometer, a spectrophotometer, or a combination thereof. In another embodiment, the deposit and patterning of said dielectrically separated crossing electrodes on said array is optimized to produce greater field strength exerted on cells trapped in said vessels.

BRIEF DESCRIPTION OF THE DRAWINGS

FIG. 4 (A-C) demonstrates pseudo-colored electron micrographs of DEP traps for holding single cells. Each trap (C) consists of four post electrodes made of gold. An array of 8 traps (B) is situated in a microfluidic chamber (A). (D) Top-down view of two viably stained HL-60 cells trapped in the dielectrophoretic traps. (E) Array of single cells trapped using p-DEP and stained with Cell Tracker Green.

FIG. 21 depicts another embodiment of an n-DEP trap design (pit diameter=30 mm). Image (A) provides a three-dimensional cartoon outlining the different layered materials requisite for fabrication (B) indicates that a 1V potential applied across the trap electrodes produces only a 0.057° C. temperature rise above ambient. The performance plots shown below the layouts outline stable holding characteristics and induced transmembrane voltages well below values known to negatively impact cell health.

FIG. 24 demonstrates one embodiment of a "mini-process" used to evaluate the Silox Vapox intermetal silicon dioxide etch step used in a fabrication process. The top portion of the chart displays the alignment mark and a pair of cross sections detailing the behavior of an ideal etch sequence. The bottom table outlines the effect of exposure to the etchant for a range of times measured as a percentage of the time recommended for a 1.5 mm thick deposited PECVD SiO2 layer. For the 100% and 150% cases no adverse effects are seen on the quality of the exposed metal surface. Even at 1000% the undercutting of the photoresist and the pocking of the metal surface are not great enough to destroy the aluminum layer. The middle table shows the actual measured etch depths for all examined data points.

DETAILED DESCRIPTION OF THE INVENTION

This invention provides, in one embodiment, a microscale sorting cytometer for screening complex phenotypes.

In one embodiment, the sorting cytometer is formed using the technology of microfabrication. Microfabrication technology, or microtechnology or MEMS, in one embodiment, applies the tools and processes of semiconductor fabrication to the formation of, for example, physical structures. Microfabrication technology allows one, in one embodiment, to precisely design features (e.g., wells, channels) with dimensions in the range of <1 mm to several centimeters on chips made of silicon, glass, or plastics. In one embodiment, the cytometer of this invention uses biologically applied microtechnology for the creation of large microscale arrays of traps that hold and sort single-cells.

Figure 2:
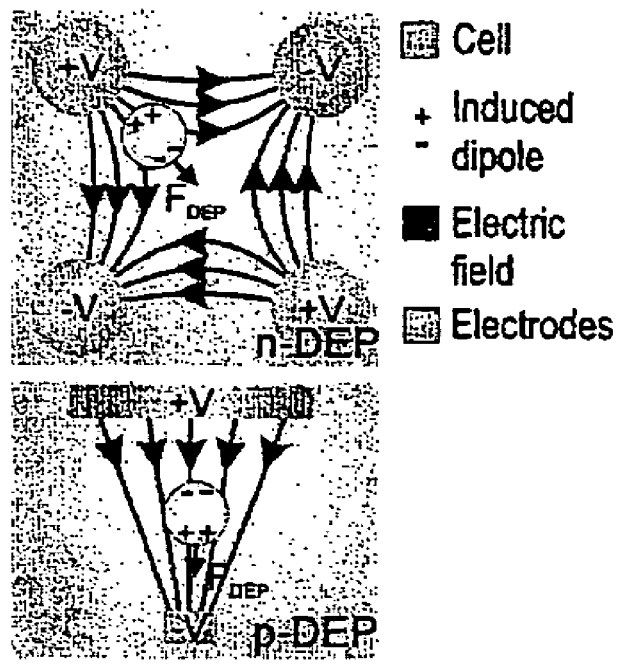
FIG. 2 schematically depicts dielectrophoretic forces exerted on a cell. (Top) Four electrodes excited as a quadrupole create a non-uniform electric field. The orientation of the induced dipole creates an n-DEP force (FDEP) away from all four electrodes, trapping the cell in the center. (Bottom) A p-DEP trap draws the cell toward the electrode with the highest electric field.

In one embodiment, electrical forces are used for manipulating cells in the methods of this invention. Electric fields can be used to manipulate cells by exerting a dielectrophoretic (DEP) force on a cell's dipole. In one embodiment, DEP refers to the force exerted on a cell in a spatially non-uniform electric field, as schematically diagrammed in FIG. 2. In one embodiment, DEP forces avoid electrode electrochemical reactions, minimize possible cellular effects, and/or create stable non-contact traps for the cells.

In one embodiment, when a cell is placed in a spatially non-uniform electric field, the electrical forces pulling on each half of the cell are unbalanced, resulting in a net force that propels the cell to either the maximum electric field intensity (positive DEP or p-DEP) or minimum field intensity (negative DEP or n-DEP). The direction of the force depends, in one embodiment, on the properties of cell, media, or applied electric field, or a combination thereof. In one embodiment, these properties are exploited for the design of a sorting cytometer, which provides traps with either configuration. In one embodiment, cells are placed in conductive media such as saline of DMEM for n-DEP; while p-DEP trap designs utilize, in another embodiment, low-conductivity buffers. In one embodiment, a DEP-based trap of this invention is amenable to microfabrication, and is in one embodiment arrayed and in another embodiment, scaled well. In another embodiment, the traps can be individually addressed because they are electrical traps. In another embodiment, the cytometer comprise traps that are effective for all types of cells. In another embodiment, the traps are so designed that they can trap cells in a variety of sizes, such as, in one embodiment, from sub-micron to, in another embodiment, tens of microns in diameter, and in according to this aspect of the invention the trap geometry is designed accordingly.

Figure 6:
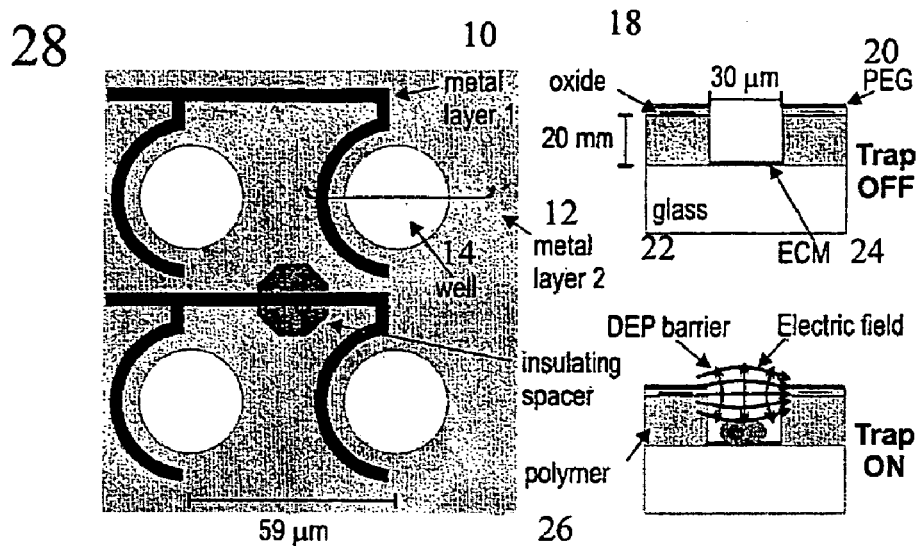
FIG. 6 demonstrates the layout (2×2 array) and operation of an embodiment of a trap 28 design in a cytometer 30 of this invention. The top view on the left shows the two metal layers 10, 12 that comprise the electrodes surrounding wells 14 formed in a polymer layer 26. The two layers are separated by an insulating spacer 16 where they cross. On the right is a side view showing how applying a voltage across the electrodes creates a DEP barrier (red) that prevents cells from escaping the well. Also shown on the right (but not on left) are the top oxide layer 18 and cell-inhibiting (PEG) 20 and accepting (ECM) 24 layers.

In one embodiment, the n-DEP trap is so designed as to be easier to fabricate, amenable to use with adherent cells, robustly trap only single cells, be able to be operated in a large array format, or a combination thereof. In one embodiment, a trap geometry may be as depicted in FIG. 6. According to this aspect, a trap 28 consists of two electrodes (metal layers 1 (10) and 2 (12)) surrounding a well 14. When energized, the electrodes create a DEP barrier that keeps trapped cells within the trap and untrapped cells out of the trap, thus ensuring robust single-cell trapping. The trap spacing is, in one embodiment, 59 mm with, in another embodiment, a 30 mm-wide well, appropriately sized to hold, in one embodiment, single NIH 3T3 fibroblasts. In another embodiment, the dimensions may be altered to accommodate other cells, which may be larger in diameter, or, in another embodiment, smaller, or in another embodiment, have a greater nucleus-to-cytoplasm ration.

Figure 7:
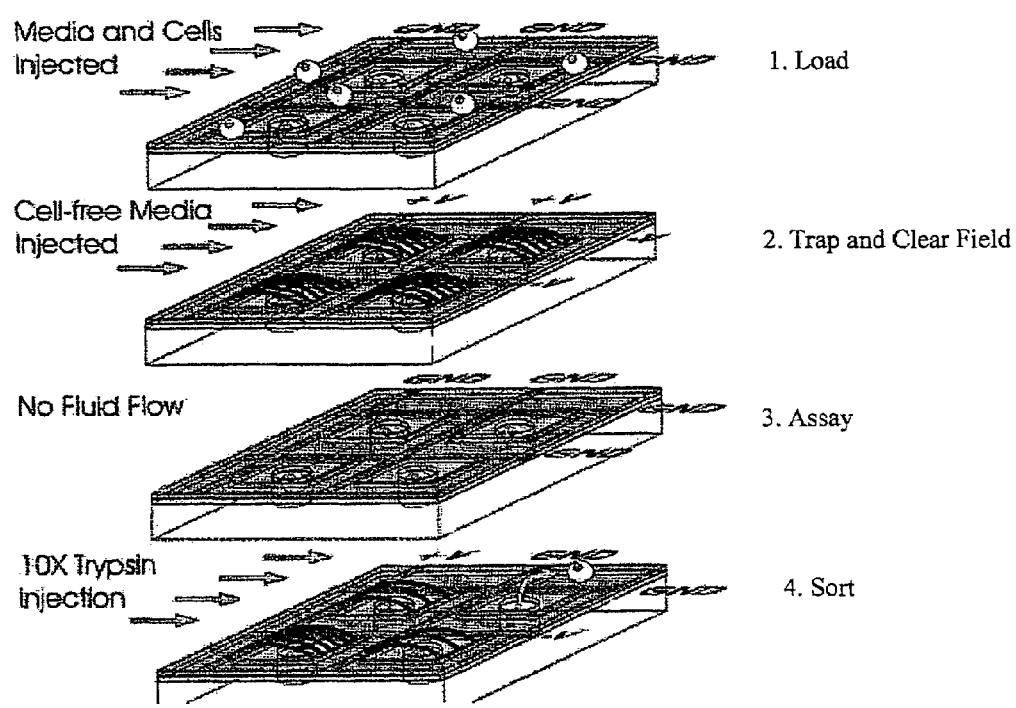
FIG. 7 depicts another embodiment of a n-DEP trap model of a sorting cytometer of this invention. Media and cells are injected through an input port, for cell loading (step 1) where cells passively enter wells. Applying voltage (step 2) initiates the cell trap, with the addition of cell-free media facilitating the clearance of the field of untrapped cells. Following grounding (step 3) all traps are disengaged, and cells remain in the wells in the absence of fluid flow, where assaying may be conducted. Specific cells may be sorted via grounding of the compartment containing a cell of interest, while concurrently initiating the traps for undesired cells (step 4). Injection of a trypsin solution facilitates dislodging of desired adherent cells.

In another embodiment, assembling a cytometer based on such a trap may be as depicted in FIG. 7. Loading of the cells occurs passively, while engagement of the traps via application of voltage, concurrent with injection of cell free media allows for clearance of the field, such that individual cells are trapped within respective wells. Grounding without fluid flow enables the passive adherence of the cells to the bottom of the wells, and sorting can be accomplished via the grounding of a well with the desired cell. Engagement of the other traps, with concurrent addition of trypsin facilitates the dislodging and removal of the desired cell, alone.

The design of the traps, in one embodiment, enables effective single cell trapping, with minimal voltage applied across the electrodes. In one embodiment, between 1 and 10V, or in another embodiment, 5 V, or in another embodiment, 2 V are applied.

In one embodiment, the electrode arrangements, forming the cellular trap comprising the sorting cytometers of this invention may include an octopole, interdigitated or castellated arrangement. In another embodiment, the DEP-based traps will have net forces created with alternating (AC) electric fields. In one embodiment, using high-frequency (100's kHz to 10's MHz) electric fields, reduces the exogenous voltage applied to the cell membrane, which can minimize cell-field interactions. In another embodiment, such a scenario prevents electrochemical reactions at the electrodes, eliminating formation of bubbles or reactive species such as hydrogen peroxide. In another embodiment, the miniaturization of the system also allays solution heating because the surface-area for heat removal increases relative to the volume for heat generation as the trap size decreases.

Figure 10:
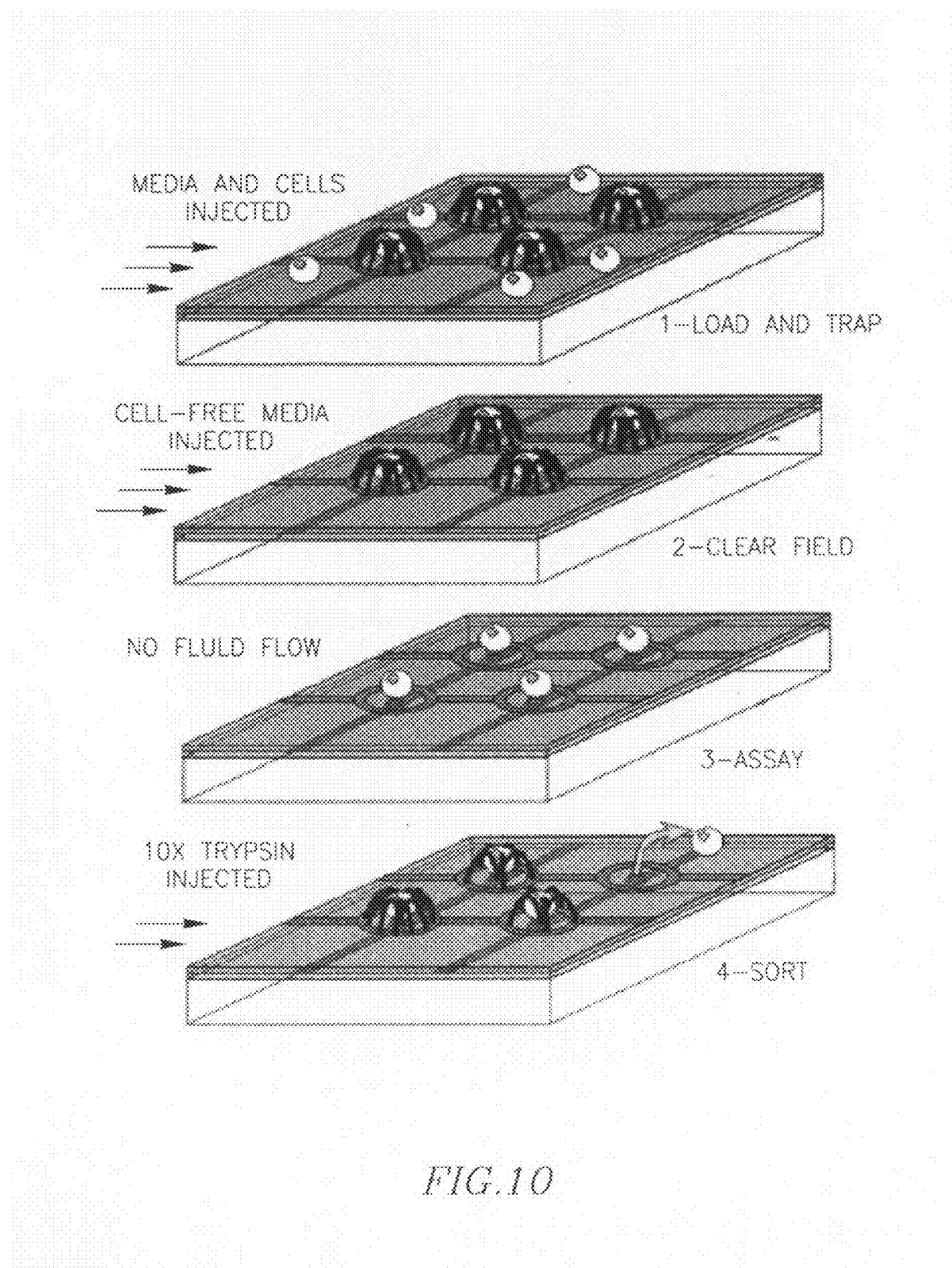
FIG. 10 depicts an embodiment of a pDEP trap 48 design in a sorting cytometer 40 of this invention. Dielectrophoretically-separated electrodes arranged in a column/row 44/46 addressing scheme facilitate trapping of attracted cells. Clearing of the field with cell free injected media (step 2), and subsequent grounding of the system ensures individual adherence of trapped cells within respective wells (step 3), where cell assay can be accomplished. Desired cells may be sorted (step 4), following grounding of traps of interest, which when trypsin is injected facilitates the cell's dislodging, allowing isolation of the cell of interest FIG. 11 demonstrates the simulated behavior of 5 different trap configurations, varied based on the geometric parameters as indicated, for the pDEP trap configuration in FIG. 10. Application of only 1 V is sufficient to provide a trap strength of up to 55 (pN), according to some designs. Temperature profiles were configured as in nDEP trap configurations FIG. 12 schematically depicts in planar and cross-sectional views, the intermetal dielectric patterning for an embodiment of componenets of a sorting cytometer of this invention. Sample results for standard microscopic evaluation of such an array are demonstrated in the lower panels, reflecting influence of etch time.

In another embodiment, a p-DEP trap may be designed that is easy to fabricate, or in another embodiment, amenable to use with adherent cells, robustly trap only single cells, or be able to be operated in a large array format or a combination thereof. In one embodiment, a trap geometry may be configured as illustrated in FIG. 10 and positioned in a sorting cytometer 40, as illustrated.

According to this aspect, the trap 48 consists of dielectrophoretically-separated electrodes arranged in a column/row 44/46 addressing scheme. When one electrode is energized, cells injected through an input port 42 are attracted and trapped within the wells. Flushing with cell free media clears the field. Grounding of the system similarly allows for cell adherence, and assay, followed by sorting which is accomplished as, for example, described in Example 3.

Figure 12:
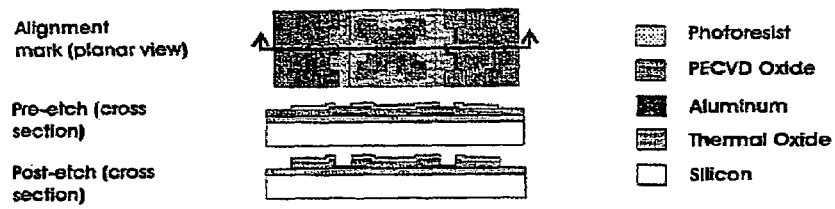

Patterning of the array for either n-DEP or p-DEP based traps for sorting cytometers can be accomplished through a variety of means. One embodiment is illustrated in FIG. 12, where the composition of the components are as indicated, and sample views by conventional microscopy are as shown.

In one embodiment, modeling software for quantitatively designing DEP traps may be accomplished, and is part of this invention. This software allows one to simulate the performance of an arbitrary three-dimensional trap given the geometry, operating parameters (voltage, frequency, etc.), fluid flow (flow profile, flow rate, etc.), and cell parameters (radius, electrical characteristics). In one embodiment, the software takes numerically calculated electric fields (from any numerical solver, for example FEMlab by COMSOL, Inc.) and imports the data into Matlab. Then, using full dielectrophoretic theory the multi-polar dielectrophoretic forces on the cell everywhere in space may be calculated, as exemplified hereinbelow. Calculating the full DEP forces allows one to accurately simulate arbitrarily complex geometries. Other forces are then calculated, depending on the situation of interest: gravitational forces, hydrodynamic drag and lift forces, etc. Once all the forces are calculated, the program may then determine, in another embodiment whether the trap stably holds the cell in those conditions by looking for stable points of zero total force using standard computational geometry algorithms.

In one embodiment, this invention provides an array architecture that is capable of being scaled to at least 10,000 traps, suitable for a real-world screen. In one embodiment, the trap geometry may be used to implement a row-column addressing scheme that will greatly increase the feasible number of trap sites. The microfabrication of a small array (4×4) of single-cell traps may be accomplished according to this aspect, and in one embodiment, provides robust single-cell trapping and release.

In one embodiment, control for on-chip traps can be accomplished using fewer than one connection/trap. In one embodiment, a more scalable architecture using a row-column addressing scheme similar to that used in LCD displays is employed in the design of the sorting cytometers of this invention. The number of off-chip connections for this type of architecture scales as $\sqrt{n}$. Thus, an array of 10,000 traps would only require 200 off-chip connections (100 rows+100 columns), a vastly more efficient arrangement. Using a trap spacing of 59 μm×59 μm, such an array would fit into a 6 mm×6 mm area. It is foreseeable that one could eventually make up to 1,000 connections, as has been demonstrated for a MEMS optical switch, leading to a 250,000 trap cytometer.

In one embodiment, designing a trap geometry that can support row-column addressing is accomplished via passively switched single-cell traps, such as exemplified the n-DEP trap of FIG. 7. The array is loaded by first flowing media-containing cells through an input port, which facilitates flow across the array and lets the cells settle into the wells (step 1). The wells are sized so that on average only a single-cell is trapped in each site. Next, all the electrodes are excited, turning ON all the traps (step 2) The application of flow while the DEP traps are ON causes all the cells on the substrate surface to be swept away while retaining the cells in the wells. Then cells are allowed to attach and the traps are turned OFF, after which the assay proceeds (step 3). It can be estimated that the total time that the cells will exposed to electric fields at ~10-30 minutes, where there is no electrical excitation during the assay; and the substrate is then passive. To effect sorting, in one embodiment, a protease (e.g., trypsin) or other dissociation buffer is introduced into the chamber and the electrodes are turned on. As the cells detach they remain trapped within the wells. They are then sorted by exciting the electrodes in a pattern that preferentially allows the desired cells to be released. The row and column corresponding to a cell to be released are set to ground (0 V). This causes the excitation at that location to cease, allowing the cell to be drawn into the flow (step 4). The released cell will not be trapped at other sites due to their DEP barriers. Importantly, cells at other sites see either a +V or +2V excitation. We can design our traps and choose our operating conditions such that +V is enough to retain the cells when flow is applied, but 0 V is not. After the cell at that row-column site has been ejected, we then set the row and column of the next site to zero excitation, repeating for each cell to be ejected. To use this trap design with cells much bigger or smaller than NIH 3T3s one may, in another embodiment, simply scale the trap geometry.

In another embodiment, the tray array may be fabricated and packaged by means well known to one skilled in the art. In one embodiment, the chips will be made out of glass wafers upon which a 20-mm thick low-autofluorescent polymer layer is spun. The two metal layers are then deposited and patterned, in another embodiment, with an interleaving oxide layer to electrically isolate the two levels. A final layer is deposited and patterned, in another embodiment, which will provide an oxide surface for further functionalization (see FIG. 6). In another embodiment, wells in the polymer layer and a flow chamber are created out of a PDMS gasket topped by a coverslip.

In one embodiment, the cytometer of this invention will be compatible with standard high-resolution fluorescence microscopes. According to this aspect, the challenges of imaging a large array of traps can take advantage of the numerous technologies that exist for high-throughput microscopy is possible. In another embodiment, because cells in our array are placed in defined locations, imaging may be faster than that accomplished in other techniques, as there is no need to "find" the cells.

In another embodiment, in order to stop any potential cell migration that might be a concern for long-term assays as well as prevent non-specific cell adsorption during the loading and sorting steps, the field of the array but not the bottom of the wells may be coated, by microstamping molecules such as polyethylene glycol (PEG) or octadecyl-trichlorosilane (OTS), both of which resist protein adhesion and are commonly used for confining cells Because the cells will be trapped within wells, using a blank microstamp to coat the surface will leave the bottoms of the wells uncoated, as desired. The chip may then, in another embodiment, be flooded with fibronectin or other ECM molecules to enhance cell attachment to the bottom of the wells (the ECM protein will not bind to the OTS or PEG region). The protein-inhibiting surface may also reduce any potential fouling of the chamber, in another embodiment.

It is possible to validate the fabricated traps and row-column addressing scheme using methods similar to those previously described [Voldman, J., Toner, M., Gray, M. L. & Schmidt, M. A. A Microfabrication-Based Dynamic Array Cytometer. Analytical Chemistry 74, 3984-3990 (2002); Voldman, J., Braff, R. A., Toner, M., Gray, M. L. & Schmidt, M. A. Holding Forces of Single-Particle Dielectrophoretic Traps. Biophys. J. 80, 531-541 (2001)]. The strength of the traps and how it correlates to modeling by trapping and releasing beads may be tested under fluid flow, as will be known to one skilled in the art, such as, for example, as presented hereinbelow in Example 6. The operating window (in terms of voltage, flow, and particle size) that allows maximal trapping of only single-particles at each site may be measured.

Operation of the cytometer with adherent cells may comprise, in another embodiment, a step including detaching attached cells before release. The conditions under which one can release attached cells in minimal time (~min) and at flowrates small enough that the detached cells can be retained by DEP traps, can be determined via methods well known to one skilled in the art.

For example, simple 200-mm high flow chambers can be constructed out of PDMS using standard techniques, and autoclaved. The flow chambers can be seeded with freshly trypsinized NIH 3T3 cells grown in standard medium (DMEM with 10% BCS, L-glutamine and antibiotics) with allowance for the cells to attach overnight. The chambers may be placed on a microscope, washed with PBS and flowed in pre-warmed trypsin (0.25% Trypsin+1 mM EDTA-4Na) at different flowrates, and the percentage of released cells over time is recorded. It is then possible to measure how quickly cells are detached under different flow conditions (e.g. determining shear stresses). In another embodiment, the cells may be exposed to short incubation periods with a trypsin solution, for dislodging the cells, after which media is flowed through the chamber, or in another embodiment, additional trypsin is flowed through the chamber for dislodging the cells.

In another embodiment, the addition of other enzymes (e.g., elastase, papain) to the dissociation mix may cleave proteins that are not digested by trypsin, or non-enzymatic dissociation buffers (including salts and chelating agents) may be used. In another embodiment, well bottoms are coated with a specific ECM protein or peptide. For instance, the RGD peptide is found in fibronectin and is the ligand for several integrins. Well bottoms coated with RGD-presenting molecules may be used, and detachment of the cells may be accomplished, in another embodiment, by competing with free RGD.

In another embodiment, sorting efficiency may be determined by using differentially labeled fibroblast populations introduced into the array in known ratios and testing that this corresponds to the observed ratios of loaded cells and that can release one subpopulation (i.e., one color) and not the other. NIH 3T3 grown in dishes, may in one embodiment, be loaded in one dish with a green fluorescent dye (e.g., CellTracker green by Molecular Probes) and another dish with an orange dye (e.g., CellTracker Orange) according to manufacturer's instructions. Then each cell population is trypsinized, resuspended in PBS, and counted with a hemacytometer. Once can then mix known ratios (1:1 to 1:1000) of each cell population at the optimum loading concentration (determined above), introduce these cells onto the chip, capture the cells, and then count each of the captured populations. Repeating several times, in one embodiment, it is expected that captured cells are in the appropriate ratios. Then release one of the populations, collection into a multi-well plate, and then release and collection of the other population may be accomplished. After releasing each subpopulation the array may, in another embodiment, be imaged, to ascertain false sorting statistics (a site whose trap is turned OFF but whose cell is not released as well as cells that are released from traps that are not turned OFF). Counting the number of recovered cells in each well of the plate will then allow a determination, for example of the sorting statistics, including % recovery of sorted cells (total # of recovered cells compared to 400 trapped cells in the array) and sorting fidelity (# of green cells in the orange microtiter well and vice versa).

In another embodiment, it may be of interest to determine whether there is an ability to recover all sorted cells without "recovering" cells that may have been "stuck" and then dislodged in the tubing somewhere. To assay these carryover effects, assays with three sets of fluorescently labeled cells (blue, green, orange) may be employed. Initially, only blue cells are introduced onto the chip and then recovered into a multi-well plate, which is repeated three times, then performed identically with green and then orange cells. By counting the number of blue cells in the green wells and blue or green cells in the orange wells it will be possible to determine any carryover effects.

In another embodiment, scaling up of the array geometry does not necessitate scaling up of the environmental and fluidic control systems. For example, the 100×100 array may be 6 mm square, which sits in a 7 mm square chamber that is 100 mm high, this gives a chamber volume of ~5 ml. Thus, a 12-hour assay that used a flowrate sufficient to change the media in the chamber once every 5 minutes would consume 720 ml of media.

In one embodiment, the cytometers of this invention comprise control systems and user interfaces. In one embodiment, control systems comprise on-chip environmental control to enable multi-hour observation of cells, electronic and fluidic control to automate the trapping process as well as the delivery of reagents to the cytometer, automated microscopy to perform observation and data acquisition, or a combination thereof. In one embodiment, all the control systems may be unified via computer interface.

In one embodiment, controlling the environment of the cytometer will enable multi-hour assays with the cells in their "preferred" environment of 37° C. with proper pH (~7.2) and oxygen tension. In one embodiment, the cell sorter cytometers of this invention may be under controlled physicochemical parameters, which may comprise temperature, pH, oxygen tension, or a combination thereof.

In one embodiment, the cell sorter cytometers of this invention may comprise an integrated temperature control system. In one embodiment, on-chip temperature sensing may be conducted, and in another embodiment, may use a microscale calibration technique that gives spatial information.

In one embodiment, the temperature control system may consist of an on-chip metal temperature-sensing resistor (fabricated at the same time as the trap electrodes) and a resistively heated transparent conductive heater connected to a computer. The computer implements in software a PID (proportional-integral-differential) controller that in turn controls a heater power supply. The transparent heater may be made, in one embodiment, of indium tin oxide (ITO), a transparent conductor that is commonly used as an electrode in LCD displays and is used as a heater in a commercial environmental chamber for microscopy (Bioptechs, Inc.). In one embodiment, it is possible to place the heater anywhere in the system.

In one embodiment, commercially obtained ITO-coated coverslips are used, and the solution is heated directly.

In another embodiment, the performance of the temperature control system can be evaluated using encapsulated thermochromic liquid crystals (TLCs) [Chaudhari, A. M., Woudenberg, T. M., Albin, M. & Goodson, K. E. Transient liquid crystal thermometry of microfabricated PCR vessel arrays. Journal of Microelectromechanical Systems 7, 345-355 (1998)]. These crystals, which are the same active ingredient found in flexible strip thermometers that patients can apply to their foreheads, change color in response to temperature differences and are readily available in formulations with responses centered around physiological temperatures and in particle sizes of several microns, giving adequate spatial resolution. They allow for the spatial integration of the image and the temperature distribution of the chip and thropugh calibration, achieving, in one embodiment, ~0.1° C. accuracy and precision.

In another embodiment, pH is controlled in DMEM-based media via a bicarbonate buffering system. In one embodiment, pre-equilibrated media is delivered to the chip, either by using a segment of gas-permeable tubing or by sparging the media in the bottle. Additionally, one can incorporate $CO_2$-filled channels on the edges of the chip to act as a barrier to outgassing from the PDMS chamber walls. In another embodiment, pH may be measured before and after the chip using a commercial inline microvolume pH sensor. One may, in another embodiment, image the flow chambers and use the phenol red indicator in DMEM to determine whether there is noticeable pH change in the medium under these conditions. If so, in another embodiment, one can adjust the $CO_2$ flowrate or thicken chamber sidewalls.

In another embodiment, $O_2$ will be monitored and controlled in the same way as $CO_2$, using inline microvolume sensing and control via media sparging, gas-permeable tubing, and/or flowing $O_2$ in channels at the edges of the chip.

In another embodiment, automatic fluid control may simplify operation of the cytometer and enable precise timing of reagent additions. The external flow system may, for example, consist of 360-mm OD tubing commonly used in HPLC coupled to computer-controlled switching and injection valves and syringe pump. One may, in one embodiment, select the inner diameter of the flow paths to minimize internal volume while preventing undue shear on the cells.

In another embodiment, electrical excitation used to operate the DEP trapping at the start and end of assay, is created and controlled at high-frequency (up to 80 MHz) voltages of up to 10 V (in case this ever proves necessary for operation).

Figure 13:
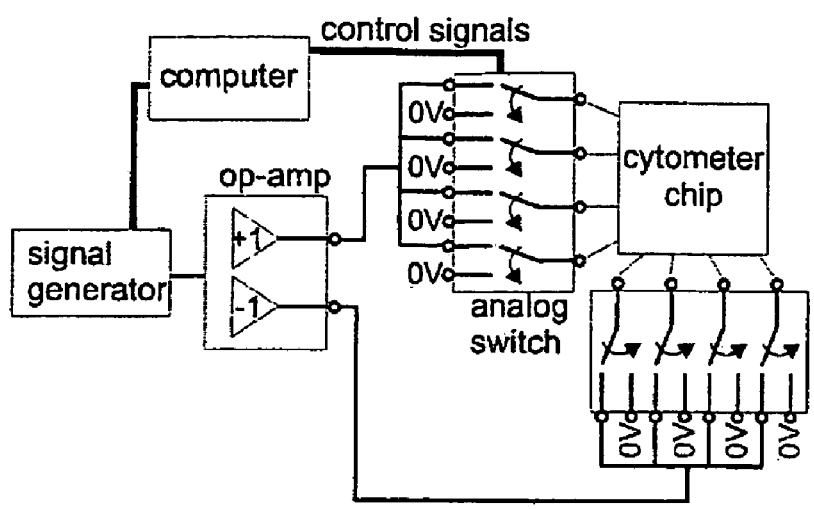
FIG. 13 depicts an embodiment of an electrical control system, which may be used in conjunction with the sorting cytometers of this invention. A signal generator creates AC sine waves that get amplified by the op-amp +1 (to make +V) or –1 (to make –V) and then goes through computer-controlled analog switches that switch the signals on and off.

In one embodiment, a schematic of the electrical control system may be as shown in FIG. 13. It consists of a signal generator—to create the voltages—that is connected to a custom printed-circuit board to amplify and switch the signals and deliver them to the cytometer. On may use, in another embodiment, commercial high-speed integrated-circuit op-amps to buffer and invert the signals, and commercial integrated-circuit analog switches to provide the row-column addressability. Both the switches and signal generator may be controlled by digital signals provided by the central computer, in another embodiment.

In another embodiment, microscopy may be used to perform imaging and phenotype acquisition in the methods of this invention. In one embodiment, commercially available, automated microscopes by Zeiss, Nikon, etc. which permit the user to control objectives, fluorescence filters, x-y stage, z-axis (autofocus), diaphragms, etc may be used. According to this aspect, appropriate control software (e.g., Metamorph) may be used, in another embodiment, to set up a timelapse protocol repeatedly taking brightfield and fluorescence pictures of an arbitrary set of fields at arbitrary time intervals.

In one embodiment, such images are used to determine the sort parameter. In one embodiment, imaging will require a tradeoff between field-of-view, spatial precision, and light-gathering ability. Increasing the objective magnification decreases the field of view, requiring more images per timepoint, but collects more light (higher numerical aperture) and thus offers faster fluorescence imaging as well as offering higher spatial resolution. For example, a trap spacing of 59 mm, in a 20×20 array will be 1.2 mm×1.2 mm, and a 100×100 array will be 6 mm×6 mm. For a typical microscope, the 20×20 array can be wholly observed with a 5× objective at 1 mm/pixel resolution.

In one embodiment, the use of two-photon microscopy will be used in order to give greater fluorescence sensitivity, or, in another embodiment, quantum dots may be used for high-brightness live-cell labeling.

In one embodiment, a combination of general assays to test overall long-term effects of cellular manipulations in the sorting methods of this invention may be conducted, which may comprise molecular analysis of the stress response using, for example, immunofluorescence or RT-PCR. In one embodiment, stress responses may be determined via the characterization of changes in both nuclear accumulation and mRNA levels in response to manipulation on-chip.

In one embodiment, stress responses may be determined as follows: trypsinized NIH 3T3 fibroblasts grown in standard medium and introduce them simultaneously into unenergized (control) and energized (at 2 V) environmentally controlled (37° C., 10% CO2) chambers on the chip. One may flow the cells onto the chip, allow them to attach, and then culture for 6 hours. To assess nuclear translocation of hsc70, one may then fix with 3.7% formaldehyde, permeabilize and perform indirect immunofluorescence in situ with an anti-hsc70 monoclonal antibody (e.g., SPA-815 from Stressgen154) and an appropriate secondary antibody. As positive controls for nuclear translocation one can use NIH 3T3 cells grown on coverslips under the same conditions that have been exposed to heat shock of 45° C. for 60 min in a water bath, conditions that have been shown to give significant nuclear translocation in HeLa cells and is more than adequate to give hsc70 upregulation in NIH3T3 cells. As negative controls one may use cells seeded on coverslips that have not been exposed to heat shock as well as cells on unenergized electrodes, to control for stress induction due to use in the microchip. Software may be used to colocalize hsc70 fluorescence with a nuclear stain such as Hoechst or DAPI using routines such as those used for the Cellomics platform.

In another embodiment, stress response may be determined via RT-PCR assay of hsc70 and hsp70 mRNA levels, both of which have been shown to be upregulated (as assayed by Northern blot) in NIH 3T3 cells in response to heat shock, for example. Trypsinized NIH 3T3 fibroblasts grown in standard medium and introduced simultaneously into six unenergized (control) and six energized (2 V) environmentally controlled chambers (this will require two chips) may be conducted. Cells attach and then are cultured for 2-12 hours. One chamber is repeatedly washed with PBS (by flowing PBS into the chamber), trypsinized, and collected cells and trypsin is inactivated with serum-containing media, and flash frozen and stored at −80° C., thawed and total RNA is isolated, for example with a commercial kit optimized for small cell numbers (e.g., Qiagen's RNAEasy micro) RT-PCR with appropriately chosen (e.g., Primer3 from Whitehead Institute), exon-spanning primers for hsc70 and hsp70 (as well as internal control such as b-actin) is performed. mRNA levels from cells on chips may be determined, as may any statistically significant increase in mRNA over time, representing heat shock induction.

Electric fields have been shown to have direct effects on cells. At the frequencies used with DEP, studies examining gross indicators of cellular physiology, such as viability, motility, doubling times, etc., have shown insignificant effects, with prevailing thought in the field being that minimizing induced transmembrane potentials (<<70 mV) and solution heating (~1° C. above 37° C.) averts gross cell-field interactions.

In one embodiment, acute cell damage due to trapping may be measured, by, for example using freshly trypsinized NIH 3T3 fibroblasts and resuspending them in media with a fluorescent live/dead viability stain (calcein AM and ethidium homodimer 1 from Molecular Probes). After a short incubation (~30-45 minutes) cell may be introduced simultaneously into unenergized (control) and energized (2 V) environmentally controlled chambers. Heat-killed fibroblasts may be used as a positive control for the dead-cell staining. Fluorescence and DIC images may be taken every few minutes during the extent of the trapping (~10-30 min), and the percent cell viability calculated as 100*(T-D)/T, where T represents the total number of cells counted in the phase contrast image and D represents the number of damaged cells.

In another embodiment, a genetic screen for proteins that affect NFAT translocation in response to intracellular calcium induction may be undertaken. According to this aspect, cell lines stably expressing NFAT-GFP reporters with which one can perform visual screens of nuclear shuttling upon addition of ionophore. Specifically, NFAT4-GFP reporter construct stably expressed in baby hamster kidney (BHK-21) cells may be used with a sorting cytometer of this invention. The reporter cell line exhibits efficient reversible nuclear shuttling (with 5-10-minute timescales) in response to elevated levels of intracellular calcium. This shuttling can be blocked, in one embodiment, with a dominant negative catalytically inactive mutant of calcineurin (DCnAH101Q), which complexes with NFAT, prevents dephosphorylation and thus translocation to the nucleus.

According to this aspect, one may reproduce nuclear translocation with these cells in conventional dishes and on the cytometer. BHK reporter cells grown in standard medium (DMEM with 10% BCS and antibiotics) are probed for nuclear shuttling by adding 1 mM of the calcium ionophore A23187, using as a negative control cells in medium containing 10 nM FK506, which blocks nuclear localization of the reporter. An expression screen is conducted, according to this aspect, using either a transiently transfected cDNA library or a retroviral cDNA library, comprising a reporter plasmid, these cells are introduced into a cytomete of this invention, allowed to attach, and cultured for a few hours (6-12 hours). Nuclear shuttling is probed by adding calcium ionophore. Specifically, cells with significant (>2 std. dev. from the mean) differences in shuttling time as well as cells in which shuttling is blocked will be individually sorted into multi-well plates for plasmid or retroviral recovery.

In one embodiment, proteins that might be identified in this screen include those directly or indirectly affect either cytoplasmic dephosphorylation or nuclear re-phosphorylation of NFAT4. Proteins known to affect translocation include inhibitors of calcineurin, such the AKAP79 scaffold protein or CAIN163, or proteins that directly or indirectly bind to NFAT4 itself, such as CKIa or MEKK1161 or JNK165. All of these would result in lack of nuclear translocation or change in shuttling dynamics upon ionophore addition Inhibitors of GSK3, which rephosphorylates NFATs in the nucleus, would lead to nuclear sequestration of NFAT4. In another embodiment, cDNAs not yet identified as belonging in the pathway may be identified via this method.

The invention provides, in one embodiment, a method for adherent cell sorting, comprising loading cells in a sorting cytometer, comprising:

a. an array;

b. a power source;

c. an input port coupled to said array;
d. vessels, with dimensions such that it holds a single cell;
e. dielectrically separated crossing electrodes coupled to said power source, surrounding said vessels arranged in a row/column addressing scheme on said array; and
f. an output port coupled to said array;

such that individual cells passively enter said vessel; applying a voltage, such that the individual cells are subjected to dieleetrophoresis, and are physically trapped within each vessel, under conditions allowing the trapped cells to adhere to the vessel; assaying adherent cells upon cessation of the application of voltage, such that a population of said adherent cells is identified whose isolation is desired; reapplying voltage to vessels comprising cells whose isolation is not desired, trapping these cells; dislodging cells whose isolation is desired, and collecting these cells from the output port. In one embodiment, non-adherent cells are sorted in a cytometer of this invention.

In one embodiment, the dielectrophoresis is positive or negative. In another embodiment, the applied voltage is between 1 and 15 V. In another embodiment, the cytometer is maintained under controlled temperature, pH, $CO_2$ or Oxygen conditions, or a combination thereof. In another embodiment, the array is comprised of a transparent material. In another embodiment, the transparent material is pyrex, quartz or SU-8. In another embodiment, the array is coated with a low-autofluorescent material. In another embodiment, the array, with the exception of the vessels, are coated with a microstamping material. In another embodiment, the microstamping material is polyethylene glycol or octadecyl-trichlorosilane. In another embodiment, the vessels are coated with a positively charged material. In another embodiment, the vessels are coated with at least one protein, which, in another embodiment, is an extracellular matrix protein.

In another embodiment, the cells comprise a vector, which, in another embodiment, comprises a reporter, which, in another embodiment, is fluorescent. In another embodiment, assaying the cells produces at least 2 distinguishable cell populations. In another embodiment, the population of adherent cells is identified by fluorescence microscopy. In another embodiment, dislodging the cells is effected by the introduction of a solution in said input port, which, in another embodiment, comprises trypsin, elastase, papain, a high salt concentration or a chelating agent, or a combination thereof. In another embodiment, the method is used for the identification of a diseased cell.

In another embodiment, this invention provides a sorting cytometer for eukaroytic and/or prokaryotic cells comprising an array; a power source; an input port coupled to the array; vessels, with dimensions such that it holds a single cell; dielectrically separated crossing electrodes coupled to the power source, surrounding the vessels, arranged in a row/column addressing scheme on the array; and an output port coupled to the array.

In another embodiment, dielectrically separated crossing electrodes on said array induce positive or negative dielectrophoresis of cells applied to said cytometer. In another embodiment, the voltage applied is between 1 and 15 V. In another embodiment, the cytometer is maintained under controlled temperature, pH, $CO_2$ or Oxygen conditions, or a combination thereof. In another embodiment, the array is comprised of a transparent material. In another embodiment, the transparent material is pyrex, quartz or SU-8. In another embodiment, the array is coated with a low-autofluorescent material. In another embodiment the array, with the exception of said vessels, is coated with a microstamping material, which, in another embodiment, is polyethylene glycol or octadecyl-trichlorosilane. In another embodiment, the vessels are coated with a positively charged material. In another embodiment, the vessels are coated with at least one protein, which, in another embodiment, is an extracellular matrix protein. array is comprised of a transparent material. In another embodiment, the transparent material is pyrex, quartz or SU-8. In another embodiment, the array is coated with a low-autofluorescent material. In another embodiment, the array, with the exception of said vessels, is coated with a microstamping material, which, in another embodiment, is polyethylene glycol or octadecyl-trichlorosilane. In another embodiment, the vessels are coated with a positively charged material. In another embodiment, the vessels are coated with at least one protein, which, in another embodiment, is an extracellular matrix protein.

In another embodiment, an illumination source is operatively positioned to direct radiation to said vessels, which is one embodiment, is a laser. In another embodiment, a beam splitter is employed with the use of said illumination source. In another embodiment, a recording device is operatively positioned to record a parameter in said cytometer. In another embodiment, the recording device is a camera, a computer, a luminometer, a spectrophotometer, or a combination thereof. In another embodiment, the deposit and patterning of said dielectrically separated crossing electrodes on said array is optimized to produce greater field strength exerted on cells trapped in said vessels.

Figure 1:
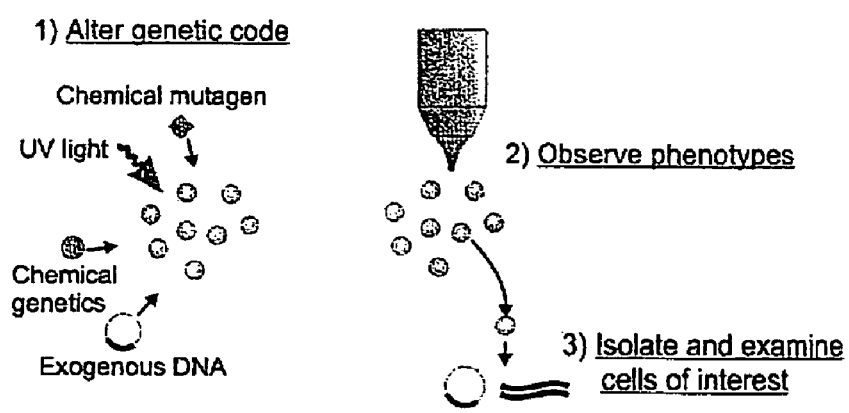
FIG. 1 schematically depicts steps comprising an embodiment of a genetic screen conducted via the methods of this invention.

In one embodiment, the screen is a genetic screen (FIG. 1), which has three fundamental steps: 1) alteration of the genetic program of the cell, 2) observation of cells for those with desired phenotypes, and 3) isolation of cells and identification of the genetic changes within the cells that are responsible for the displayed phenotypes. The first step can be accomplished in many different ways, including, in one embodiment, using the natural (background) mutation rate, or, in another embodiment, inducing mutations with chemicals or UV light, or in another embodiment, introducing exogenous pieces of DNA (e.g., transfection), or, in another embodiment, using small molecules or siRNAs to alter protein function or, in another embodiment, protein expression. In one embodiment, us of a cytometer of this invention, to image cells over time and then isolate cells of interest, will dramatically enhance the reach of genetic screens.

In another embodiment, screening and retrieval of cells via the methods of this invention enable detection of complex phenotypes: behaviors that vary over space (within the cell) and over time. Cells are inherently dynamical systems with specialized compartments. Timescales for relevant phenomena vary over many orders of magnitude, from the subsecond responses of cells to calcium, to the 10's of seconds for ligand-induced protein translocation, to the hours needed for mammalian cells to go through the cell cycle, and each of these timescales may be observed via the methods of this invention.

Cells (especially eukaryotic cells) are also compartmentalized systems. Transcription occurs in the nucleus, secreted proteins are processed in the Golgi, and mitochondria produce ATP. Thus, knowing a protein's location gives vital information as to its function. In addition, protein localization is dynamic; proteins shuttle from the membrane to the cytoplasm upon receptor activation, traffic through the Golgi during processing, or shuttle into the nucleus to activate transcription. Thus, temporal patterns of intracellular localization give information as to the dynamics underlying cell function; a protein of unknown function localized to the mitotic spindle during M phase is likely involved in mitosis. In another embodiment of this invention, assaying the cells via the methods of this invention, include assessment of cellular compartmentalization of a protein of interest, its spatial arrangement over time, and interaction with other cellular protein and/or nucleic acids.

In one embodiment, the genetic screens conducted via the methods of this invention will use cells with fluorescent outputs, such as green fluorescent protein (GFP) or its variants [Tsien, R. Y. The green fluorescent protein. Annual Review of Biochemistry 67, 509-544 (1998)], that indicate, or report, the presence of the phenotype of interest [Taylor, D. L., Woo, E. S. & Giuliano, K. A. Real-time molecular and cellular analysis: the new frontier of drug discovery. Current Opinion in Biotechnology 12, 75-81 (2001); Rutter, G. A., Kennedy, H. J., Wood, C. D, White, M. R. H. & Tavare, J. M. Real-time imaging of gene expression in single living cells. Chemistry & Biology 5, R285-R290 (1998)]. In one embodiment, screens of protein subcellular localization [Rolls, M. M. et al. A visual screen of a GFP-fusion library identifies a new type of nuclear envelope membrane protein. J Cell Biol 146, 29-44. (1999); Peelle, B. et al. Intracellular protein scaffold-mediated display of random peptide libraries for phenotypic screens in mammalian cells. Chem Biol 8, 521-34. (2001; Fujii, G., Tsuchiya, R., Ezoe, E. & Hirohashi, S. Analysis of nuclear localization signals using a green fluorescent protein-fusion protein library. Exp Cell Res 251, 299-306. (1999)], two-hybrid screens for protein interactions [Shioda, T., Andriole, S., Yahata, T. & Isselbacher, K. J. A green fluorescent protein-reporter mammalian two-hybrid system with extrachromosomal maintenance of a prey expression plasmid: application to interaction screening. Proc Natl Acad Sci USA 97, 5220-4. (2000)], and reporters of protein tyrosine kinase activity [Ting, A. Y., Kain, K. H., Klemke, R. L. & Tsien, R. Y. Genetically encoded fluorescent reporters of protein tyrosine kinase activities in living cells. Proc Natl Acad Sci USA 98, 15003-8. (2001)] may be effected via visual inspection of fluorescing cells, as described. Fluorescence may also used to study the intracellular dynamics of the cells within the cytometers of this invention. In one embodiment, fluorescence resonance energy transfer (FRET), which is a sensitive measure of protein-protein interactions, and has been used to study everything from protein localization to kinase activity [Lippincott-Schwartz, J., Snapp, E. & Kenworthy, A. Studying protein dynamics in living cells. Nat Rev Mol Cell Biol 2, 444-56. (2001); Zhang, J., Campbell, R. E., Ting, A. Y. & Tsien, R. Y. Creating new fluorescent probes for cell biology. Nat Rev Mol Cell Biol 3, 906-18 (2002)] may be employed in the methods of this invention. In another embodiment, fluorescence recovery after photobleaching (FRAP), may be used to measure protein mobility by, in one embodiment, photobleaching a cell area and measuring the time needed to restore fluorescence from newly introduced fluorophores. In another embodiment, fluorescence correlation spectroscopy (FCS) may be used to measure protein diffusion and concentration in live cells, giving information on, in another embodiment, protein-protein interactions.

In another embodiment, morphology is another phenotypic indicator used in the methods of this invention. In another embodiment, morphological assessment may be complemented with molecular characterization. In another embodiment, morphology is utilized in characterizing cell function, such as for example, and in another embodiment, the determination of cellular apoptosis, which may be determined morphologically, via the observation changes in cell and nuclear morphology over the time course of the process studied.

In one embodiment of this invention, the sorting cytometer combines the versatility of microscopy with the automated sorting capability of flow cytometry. In one embodiment, a sorting cytometer of this invention may screen 10,000 cells simultaneously. In another embodiment, the sorting cytometer of this invention may be used in conjunction with automated sorters, such as, in one embodiment, a FACS sort to enrich for cells, for example, that have been transfected with a reporter, such as, in another embodiment, a GFP-containing plasmid, followed by assay in the microfabricated sorting cytometer, which may then be used to screen, in another embodiment, for dynamic behavior of the expressed protein. In another embodiment, the cytometer is compatible with attachment-dependent mammalian cells because most mammalian cells are in this class and this allows investigation into attachment-dependent processes (e.g., focal adhesions).

In another embodiment, one-step library screens, such as, in one embodiment, a cDNA or mutant library, of mammalian cells having undergone transient transfections with such libraries may be performed. In another embodiment, screens involving introduced genetic elements using, in one embodiment, stable transfection or in another embodiment, transient transfection with pooled libraries, may be used. In another embodiment, a cytometer of this invention can be used to isolate single positive-responding cells for immediate genetic analysis, such as, for example, single-cell PCR.

In another embodiment, fluorescent reporters based on FRET, which experience a shift in fluorescence emission wavelength (typically blue to yellow) after activation, may be used in the methods of this invention. The change in fluorescence (the fluorescence ratio) serves as the reporter, and in one embodiment, screening according to this aspect may be accomplished via observing the same cell twice—before and after activation—to measure the change in fluorescence. Rationally designed FRET reporters or those generated in reporter libraries via random mutagenesis may be used, in one embodiment.

In another embodiment, synthetic genetic regulatory modules introduced into, for example, *E. coli* may be used to investigate genetic regulation and fundamental cell biology, via the methods of this invention. In one embodiment, combinatorial techniques to generate plasmids randomly encoding differing two-input (the small molecules IPTG and aTc) and one output (a GFP reporter) logic functions, may be used as described [Guet, C. C., Elowitz, M. B., Hsing, W. & Leibler, S. Combinatorial synthesis of genetic networks. Science 296, 1466-70. (2002)]. In one embodiment, similar library-based approaches could be extended to dynamic (or even localization) circuits (such as variations on the original repressilator) where cells are easily isolated after extended dynamic monitoring In another embodiment, phage display is used to engineer antibodies or other proteins with specific properties (e.g., high-affinity binding of ligand), whose binding may be determined via the methods of this invention. In one embodiment, engineered enzymes, which produce diffusible products may be assessed via the methods and utilizing the cytometers of this invention, such as via, in one embodiment, visualization of a ligand that became fluorescent after enzymatic processing, wherein one could screen for a diffuse fluorescent cloud around cells and thus assay enzymatic activity. In one embodiment, according to this aspect, strongly fluorescent clouds would then indicate enzymes with rapid kinetics, which could then be isolated and undergo further rounds of evolution.

In another embodiment, combining fluorescence reporter output (fluorescence intensity) with localization greatly enhances the capability of cell-based screens. In one embodiment, high-throughput genetic screens for investigating the secretory pathway with a VSVG-GFP reporter could be used to find proteins that affect various steps in this pathway. In one embodiment, specific inhibitors of Golgi-to-membrane trafficking, such as for example, secramine, may be isolated via chemical genetic screen, performed via the methods of this invention. In one embodiment, a translocation-based screen may be conducted using a cytometer of this invention. In one embodiment, a fluorescent NFAT reporter that translocates to the nucleus upon activation may be used to screen a cDNA library for proteins that disrupt this pathway, wherein the imaging and isolation of positive-responding cells is conducted via the methods of this invention.

In another embodiment, the microfabricated format of the cytometer of this invention may be utilized to functionally probe cells, in conjunction with other cellular probe machinery. In one example, the sorting cytometer of this invention may be modified to include the ability to perform on-chip patch clamping, which allows one to functionally screen transiently transfected ion-channel libraries. In another embodiment, real-time nanoscale sensors and other microfluidic-based technologies may be incorporated within the cytometers of this invention.

EXAMPLES

Example 1

DEP-based Cellular Trap

In order to design a DEP trap that works well enough to be scaled to a large array, unique modeling software for quantitatively designing DEP traps was developed. This software allows one to simulate the performance of an arbitrary three-dimensional trap given the geometry, operating parameters (voltage, frequency, etc.), fluid flow (flow profile, flow rate, etc.), and cell parameters (radius, electrical characteristics). The software took numerically calculated electric fields (FEMlab by COMSOL, Inc.) and imported the data into Matlab. Then, using full dielectrophoretic theory, the multi-polar dielectrophoretic forces exerted on the cell everywhere in space was calculated, which allowed for the accurate simulation of arbitrarily complex geometries. Other forces may also then be calculated, depending on the situation of interest: gravitational forces, hydrodynamic drag and lift forces, etc. Once all the forces were calculated, the program determined whether the trap stably holds a cell in those conditions by looking for stable points of zero total force using standard computational geometry algorithms.

Figure 3:
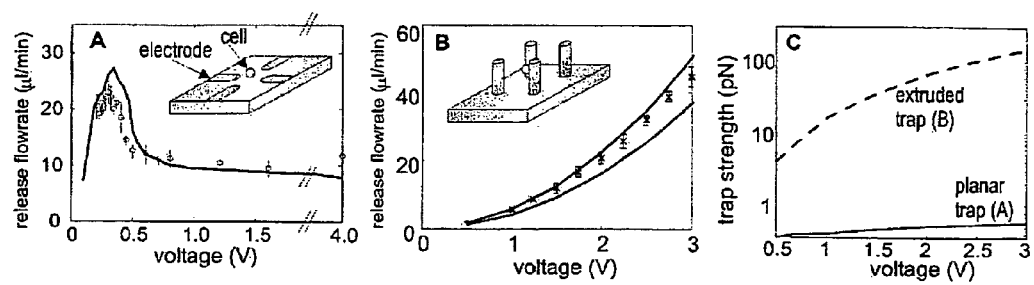
FIG. 3 demonstrates the modeling of DEP traps. (A) Comparison between modeling (–) and experiments (o) for holding of 10-mm diameter beads in planar quadrupole traps (shown in inset). Plotted is the flowrate needed to release the beads as a function of applied voltage2. (B) Same as A, but for extruded quadrupole traps. The two lines for modeling show the range of predicted outcomes based upon variations in the device geometries. The measured release flowrates are numerically similar to (A), but because the flow chamber has a different geometry this trap is much stronger than in (A). (C) Comparison between trap strength extracted from the models for both planar (A) and extruded (B) traps, showing that the extruded traps are >100× stronger for V>~2V.

Using this modeling software an analysis was conducted on the performance of simple planar quadrupole traps, formed by depositing and patterning thin metal electrodes and exciting them in a quadrupolar fashion (FIG. 3A). The software predicted to within 30% absolute error, the performance of these traps in holding polystyrene beads (beads are used to validate the trap performance because of their uniform and well-defined properties). The modeling software was then used to design a much stronger trap that used extruded electrodes (inset of FIG. 3B), whose performance is shown in FIG. 3B. FIG. 3C shows an extracted comparison of the strength of these two traps, showing that the extruded trap is >100× stronger than the planar trap. Thus computer modeling as described herein, wherein all input parameters were measured, given by the manufacturer, or deduced from the literature enabled the design of superior traps for construction of a cytometer.

Example 2

Functional DEP-Based Sorting Cytometers

The traps designed in the modeling step of Example 1 were then constructed, and are shown in FIG. 4. These traps were designed for non-adherent mammalian cells (leukocytes). The traps were created on a glass (Pyrex) substrate, and consisted of electroplated gold post electrodes atop a 0.5 mm-thick Ti/Au interconnect layer. The traps were enclosed in a 150-mm high flow chamber with a polymer gasket (made of SU-8 photoresist) that was capped with a coverslip to allow high-fidelity optical access. With this array, capture, holding, and arbitrary sorting of individual HL-60 cells was accomplished. In addition, cultured HL-60 cells, were resuspended in PBS, trapped in the cytometer and then calcein was introduced into the chamber and the cytometer was imaged for 45 minutes, after which cells were sorted.

Figure 5A:
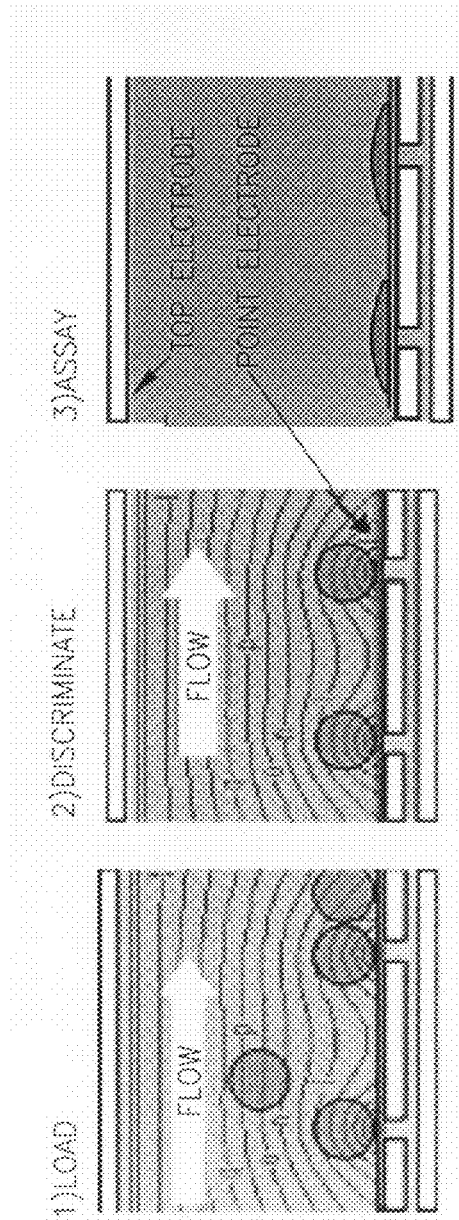
FIG. 5 demonstrates p-DEP traps according to an embodiment of this invention. (A) Side-view schematic of trap operation. Cells are first flowed into the chamber, wherein they are drawn toward the high-field regions near the bottom electrode points (1). Excess cells are flowed away (2), and the traps are turned off, the cells attach and assay proceeds (3). (B) Fluorescent micrograph of array of endothelial cells. (C) Schematics and micrographs showing independent patterning of fibroblasts and fibronectin. Independent patterning of a confining fibronectin region prevents cells for migrating away.
Figure 5C:
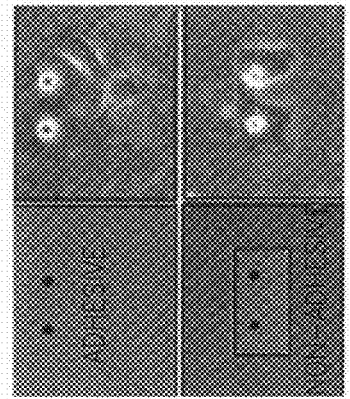
Figure 5B:
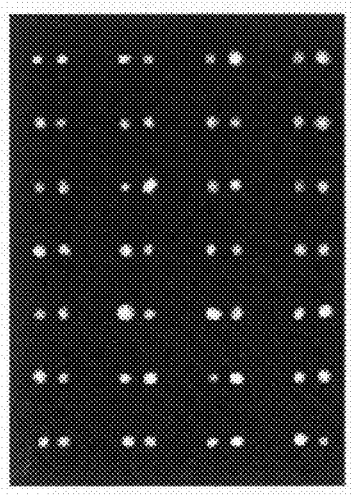

Traps that use DEP to independently pattern cells and extracellular matrix were developed as well. As shown in FIG. 5A, traps consisting of two electrodes, a top transparent electrode on the coverslip and a point electrode on the substrate may be designed. The cells experience p-DEP in this system and are thus drawn to the non-uniform electric field at the points and are trapped there, in large arrays if needed (FIG. 5B). Furthermore, cells can be patterned independently of ECM, as shown in FIG. 5C, where fibronectin is patterned around the points, allowing one to confine two fibroblasts.

Example 3

Scalable nDEP-based Traps

The design of an n-DEP trap that would be easier to fabricate, amenable to use with adherent cells, robustly trap only single cells, and be able to be operated in a large array format was undertaken. In conjunction with the design, the modeling software was extended in order to predict temperature rises during trapping. FIG. 6 demonstrates another trap geometry, which meets these requirements.

The trap 28 consists of two electrodes (metal layers 1 (10) and 2 (12)) surrounding a well 14. When energized, the electrodes create a DEP barrier that keeps trapped cells within the trap and untrapped cells out of the trap, thus ensuring robust single-cell trapping. The trap spacing is 59 mm with a 30 mm-wide well, appropriately sized to hold single NIH 3T3 fibroblasts.

Assembling a cytometer based on such a trap may be as depicted in FIG. 7. Loading of the cells occurs passively, while engagement of the traps via application of voltage, concurrent with injection of cell free media allows for clearance of the field, such that individual cells are trapped within respective wells. Grounding without fluid flow enables the passive adherence of the cells to the bottom of the wells, and sorting can be accomplished via the grounding of a well with the desired cell. Engagement of the other traps, with concurrent addition of trypsin facilitates the dislodging and removal of the desired cell, alone.

Figure 8:
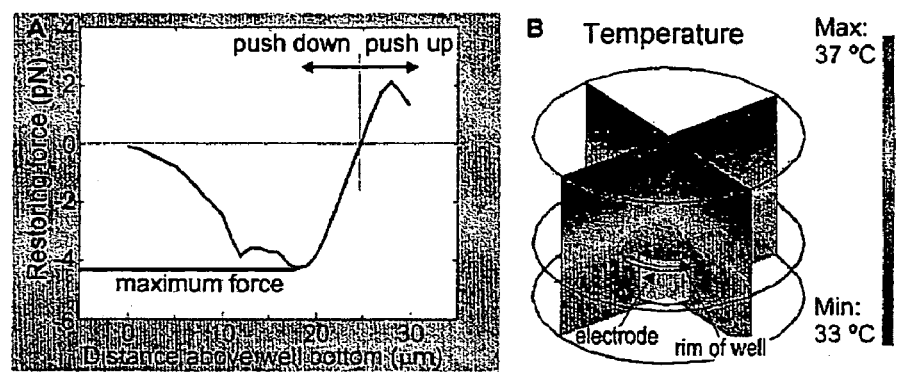
FIG. 8 schematically depicts an embodiment of a Continuous Fiber Electrochemical Actuator 76 comprised of a fiber composite system, in which the active fibers form the anode 78. The fiber anode is separated from the cathode 80, by a polymer or inorganic separator 82, and a liquid or solid electrolyte layer 84. Current collectors 86 and 88, respectively, are connected to the power source 90 in the actuator.

The performance of the trap of FIG. 6 was modeled using the modeling software. Results predicted that single cells could be held in such a trap with only 2 volts applied across the electrodes at 80 MHz, corresponding to an average field strength $10^5$ V/m. At this voltage cells predictably could be held against fluid flows of 25 ml/min (in a 100 mm high×5 mm wide chamber), corresponding to a holding force of ~4 pN (FIG. 8A), which is twice the flow possible using the extruded trap geometry shown in Example 2, The reason for this increased performance is that the cell location shields them from the largest flow forces. The calculated temperature profile is shown in FIG. 8B, with a maximum temperature rise of 4° C. above ambient. Importantly, the overall chamber temperature can be set to 33° C. to ensure that the cells are at 37° C. It should be noted that the model assumes a worst-case thermally insulating glass substrate; the actual temperature rises may be smaller due to the significant thermal conductivity of glass.

Figure 9A:
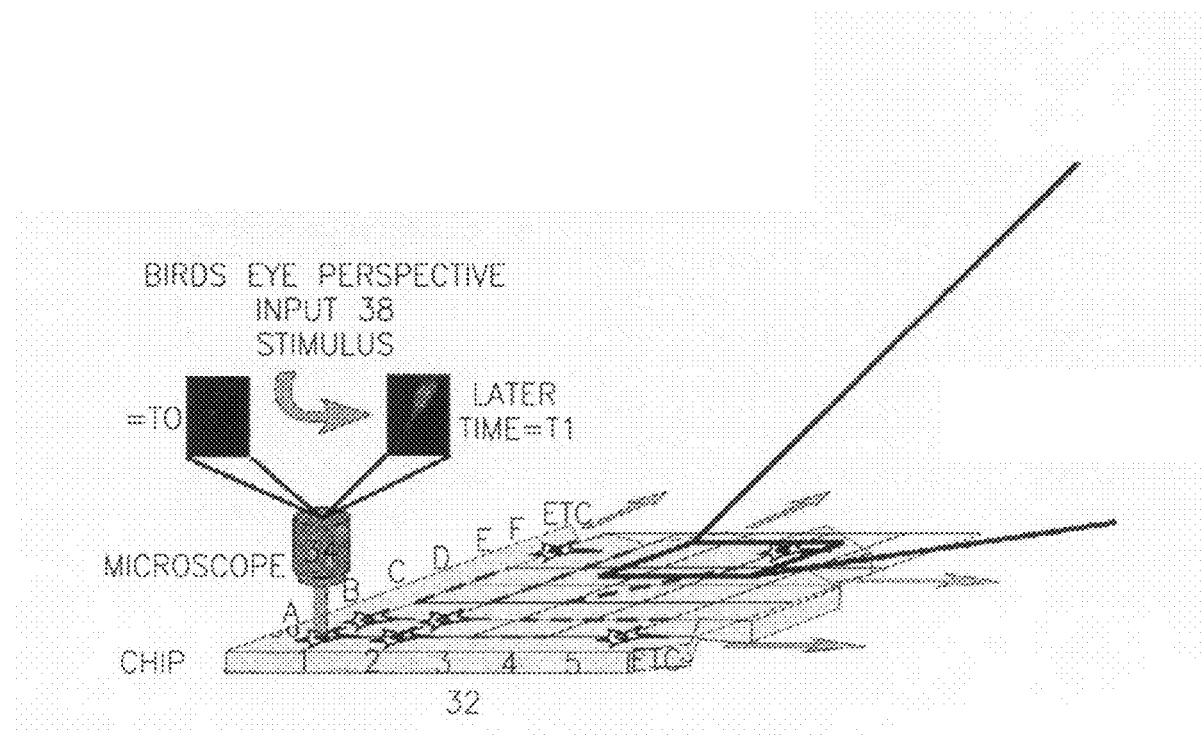
FIG. 9 demonstrates the performance metrics for an nDEP trap design according to FIG. 7.
Figure 9B:
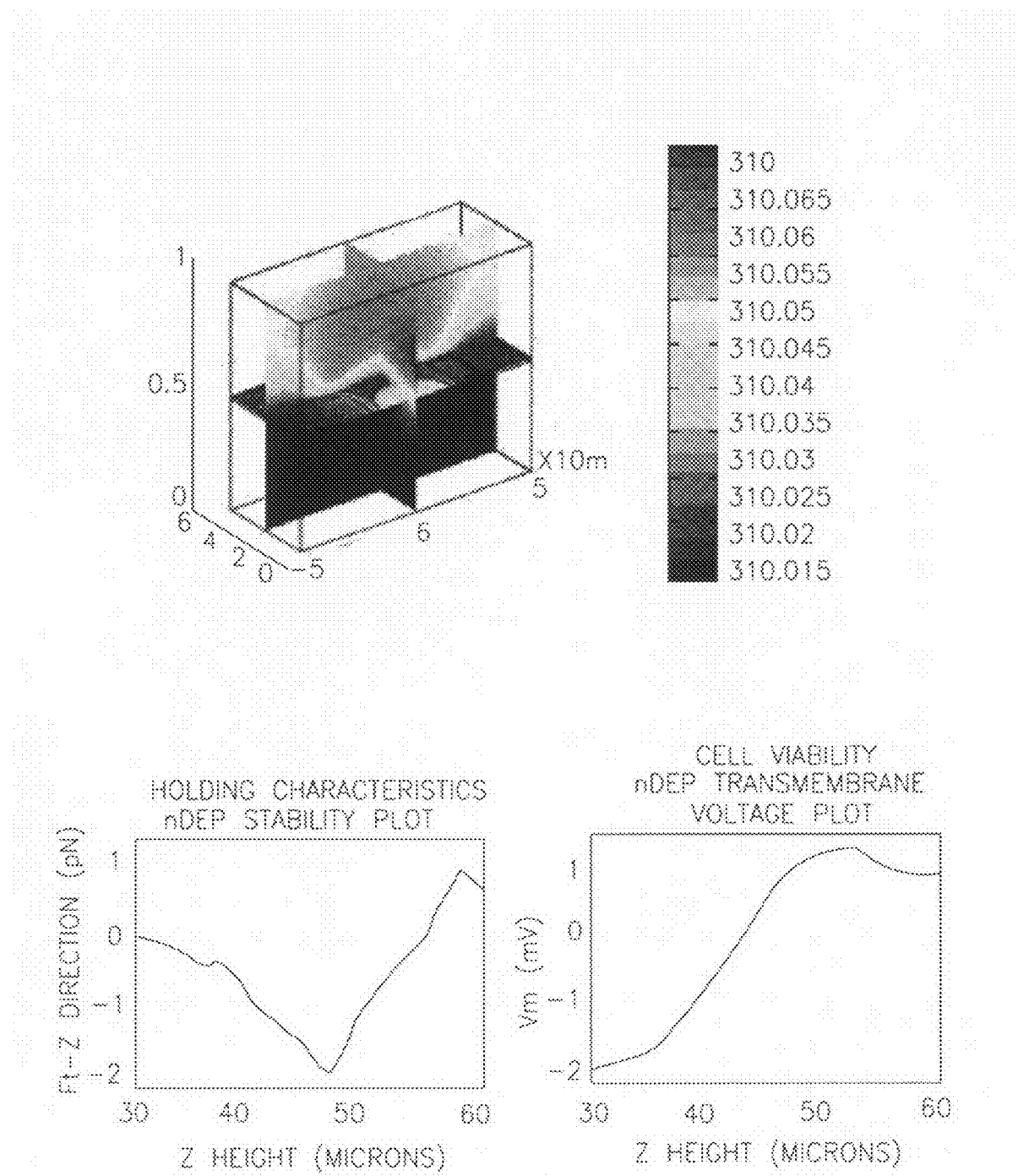

Similarly, FIG. 9 demonstrates the design and performance metrics of the nDEP trap design of FIG. 7. Temperature profile, holding characteristics are comparable to that seen in FIG. 8, with cell viability being an additional factor that may be assessed in the proposed system.

Example 4

Scalable nDEP-based Traps

The design of a p-DEP trap that would be easier to fabricate, amenable to use with adherent cells, robustly trap only single cells, and be able to be operated in a large array format was also undertaken. In conjunction with the design, the modeling software was extended in order to predict temperature rises during trapping. FIG. 10 demonstrates another trap geometry positioned in a sorting cytometer 40, which meets these requirements.

The trap 48 consists of dielectrophoretically-separated electrodes arranged in a column/row 44/46 addressing scheme. When one electrode is energized, cells injected through an input port 42 are attracted and trapped within the wells. Flushing with cell free media clears the field. Grounding of the system similarly allows for cell adherence, and assay, followed by sorting which is accomplished as in Example 3.

Figure 11:
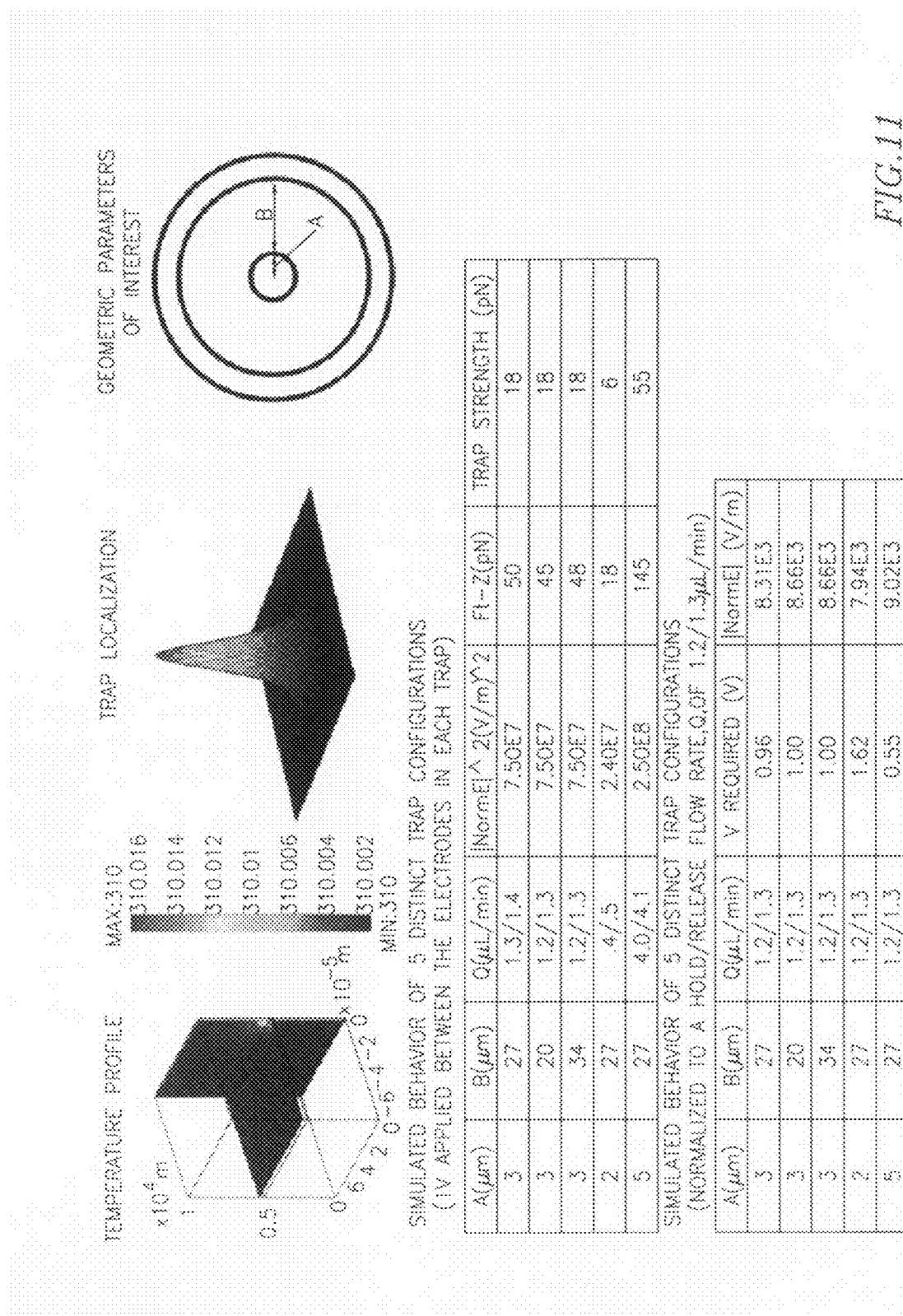

The performance of the trap of FIG. 10 was modeled using the modeling software. Results are presented in FIG. 11, which predicts the parameters for 5 different configurations of the trap.

Patterning of the array for either n-DEP or p-DEP based traps for sorting cytometers can be accomplished through a variety of means. One example is illustrated in FIG. 12, where the composition of the components are as indicated, and sample views by conventional microscopy are as shown.

Example 5

Factors Involved in Trap Design

Estimating Cell Diameter

3T3 murine fibroblasts were cultured in 100 mm dishes (Corning, Corning, N.Y.) using a media solution comprised of 87% Dulbecco's Modified Eagle Medium (Gibco, Carlsbad, Calif.), 10% fetal calf serum (VWR, West Chester, Pa.), 2% L-glutamine (200 mM, 100×—supplied at 29.2 mg/mL in 0.85% NaCl) (Gibco, Carlsbad, Calif.), and 1% penstrep (10,000 units/mL penicillin G sodium, 10,000 μg/mL, of streptomycin sulphate) (Gibco, Carlsbad, Calif.). These cells were incubated at 37° C. in a 5% $CO_2$ atmosphere using a Steri-Cycle $CO_2$ incubator (ThermoForma, Marietta, Ohio). When cultures reached densities of approximately $10^6$ cells/mL, cells were exposed to a five-minute incubation with Trypsin-EDTA (1×0.25% Trypsin with EDTA-4Na, prepared with 2.5 g Trypsin 1:250 and 0.38 g EDTA-4Na/L in HBSS without Ca++ and Mg++) (Gibco, Carlsbad, Calif.), after which trypsin was quenced with fresh media. Cells were titrated, re-plated into fresh 100 mm dishes, and photographed using a Spot RT Color camera (Diagnostic Instruments, Sterling Heights, Mich.) set to record phase-contrast grayscale images and through a 10×/0.30 Plan Neofluar objective (Zeiss, Thornwood, N.Y.) mounted on an Axiovert 200 inverted microscope (Zeiss, Thornwood, N.Y.). Imaging the cells at the onset of a culture cycle, prior to surface attachment, afforded their viewing in the most spherical form. Photoshop software suite (Adobe Systems, San Jose, Calif.) was used to extract average diameter values, in pixel counts, for a host of different cells in the images acquired. A rough estimate of the physical length associated with pixel counts, using two separate metrics, was obtained.

For the estimate, a micromachined grating (Edmund Industrial Optics, Barrington, N.J.) with sets of chrome lines patterned in densities varying between 10 and 55 lines per millimeter (stepped in increments of 5 lines per millimeter) and a set of polystyrene beads (Bangs Laboratories, Fishers, Ind.) with engineered diameters of 9.7, 14.15, and 19.5 microns were evaluated. Using the grating measurement tool, an average pixel to micron ratio of 3.2 was obtained across the entire range of line densities listed above (one measurement taken for each density). For each of the polystyrene bead sizes three separate measurements of pixel counts associated with bead diameters were conducted. These measurements resulted in a pixel to micron ratio of 3.4. Averaging the ratios from the two different calibration approaches provided a method for converting cell diameters as measured in pixels to corresponding physical distances.

Size estimates for cells for use in designing DEP electrodes was needed for optimizing trap design. In this context, estimates for the NIH 3T3 line were undertaken. To evaluate different electrode footprints and their associated DEP trapping potentials, numerical simulations using two separate software packages were conducted. Three-dimensional renderings of the trap electrodes and neighboring materials were constructed using either the Femlab 2.3 or 3.0 (Comsol, Burlington, Mass.) multi-physics plug-in for Matlab (The MathWorks, Natick, Mass.). With the geometries established, material properties (electrical and thermal) were then assigned to the individual components in designs. Boundary conditions for all surfaces in the layout were set, and then sequentially initiated electroquasistatic and heat flow solvers were added to generate electric field data and temperature profiles for each configuration tested. The electric field data was then exported for each design to a Matlab workspace and an assortment of simulations were conducted [Voldman, J., A Microfabricated Dielectrophoretic Trapping Array for Cell-based Biological Assays, in EECS. 2002, MIT: Cambridge, Mass. p. 152] to render DEP force fields. The temperature profiles, in conjunction with the Matlab simulation work, outlined the performance characteristics of the evaluated designs. Various stability parameters and field induced cellular effects were plotted.

Computing the Electric Field

In general, determining the electric field associated with a given electrical system is done through application of Maxwell's equations. In this case, the electroquasistatic approximation of the equations was implemented, a simplification (see Table 1), which modifies Faraday's differential law to neglect the influence of magnetic induction in the system. The approximation was appropriate for the simulation of the designs tested as it applies to situations where the electric field is the primary field in the system and wave phenomena associated with the lag between voltage sources and their corresponding electric fields is negligible.

TABLE 1

Outline of Maxwell's equations and the corresponding electroquasistatic reduction

| Name | Full Form | Electroquasistatic Form |
|---|---|---|
| Gauss' Law | $\nabla \cdot \epsilon_o E = \rho$ | $\nabla \epsilon_o E = \rho$ |
| Ampere's Law | $\nabla \times H = J + \dfrac{\partial \epsilon_o E}{\partial t}$ | $\nabla \times H = J + \dfrac{\partial \epsilon_o E}{\partial t}$ |
| Faraday's Law | $\nabla \times E = -\dfrac{\partial \mu_o H}{\partial t}$ | $\nabla \times E = -\dfrac{\partial \mu_o H}{\partial t}; 0$ |
| Magnetic Flux Continuity | $\nabla \cdot \mu_o H = 0$ | $\nabla \cdot \mu_o H = 0$ |

For irrotational field systems described by the electroquasistatic approximation [Haus, H.A.a.J.R.M., *Electromagnetic Fields and Energy.* 1989, Englewood Cliffs, N.J.: Prentice Hall. 742] it can be shown that $$E = -\nabla \Phi \qquad \text{[Eqn. -1]}$$

where $\Phi$ is the potential.

Inserting this equation back into Gauss' law provides the Poisson relation $$\nabla^2 \Phi = -\frac{\rho}{\varepsilon_o} \qquad \text{[Eqn. -2]}$$

where $\rho$ is the charge density and $\varepsilon_o$ is the permittivity of free space. This expression simplifies to the Laplace relation (see Eqn. 3) for cases, such as those in the trap geometries, where there are no free charges.

$$\nabla^2 \Phi = 0 \qquad \text{[Eqn. -3]}$$

By applying the appropriate system boundary conditions one can then evaluate the electric potential everywhere in the system and then back out the corresponding electric fields using the relation listed in Eqn. 1.

Resolving Temperature Profiles

Since electric fields used in the DEP traps may serve as a source for rises in temperature in media surrounding the electrodes, both electric field determinations and temperature changes were calculated. Finite Element Analysis (FEA) was used for the numeric determination of electric field data, which is suited for use in applications where the system is largely inhomogeneous in composition. The corresponding volume heat generation in the media was then determined, where the injected heat on a per volume basis Q is described by the Eqn. 4:

$$Q = \frac{1}{\sigma}|J|^2 = \frac{1}{\sigma}|\sigma E|^2 = \sigma|\nabla V|^2 \qquad \text{[Eqn. -4]}$$

where $\sigma$ is the electrical conductivity and J is the current density. Incorporating this equation into the subdomain description for the reservoir of media sitting atop the trap electrodes rendered the temperature profiles for some of the designs examined, by translating field data into an associated thermal response.

Large temperature rises above 37° C. affect cell behavior, and may also produce electrohydrodynamic flows, which are caused by large temperature gradients. Carefully restricting the temperature allowances simplified the design process and ensured that DEP forces were the dominant field-promoted system response.

Figure 14:
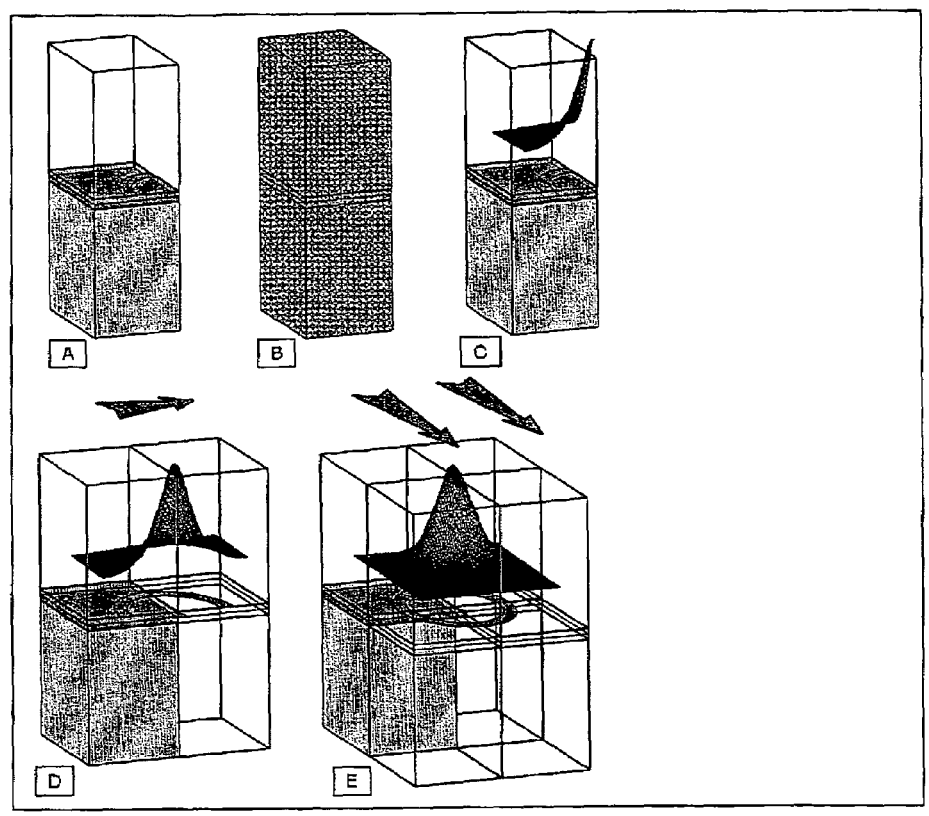
FIG. 14 depicts the sequence of steps performed in the Femlab simulation environment for an example trap design possessing two degrees of symmetry. (A) shows a ¼ model of the geometry, while (B) provides its associated finite element mesh and (C) offers the normalized electric field solution. Pictures (D) and (E) present visuals of the Matlab matrix manipulations necessary for generating a full electric field solution for the trap. (D) shows the reflection in the x-direction, and (E) gives the reflection in y-direction.

A portion of the model was then simulated, the associated field data was ported to a Matlab workspace and a series of matrix concatenations was performed to construct a full model description (FIG. 14). The half-model layouts required one reflection across a single plane of symmetry while the quarter models mandated reflections in both the x and y directions. Electrode thickness was not considered, which enabled reduction of the number of discrete elements needed to characterize a given architecture, permitting fewer equations in the system description.

Figure 15:
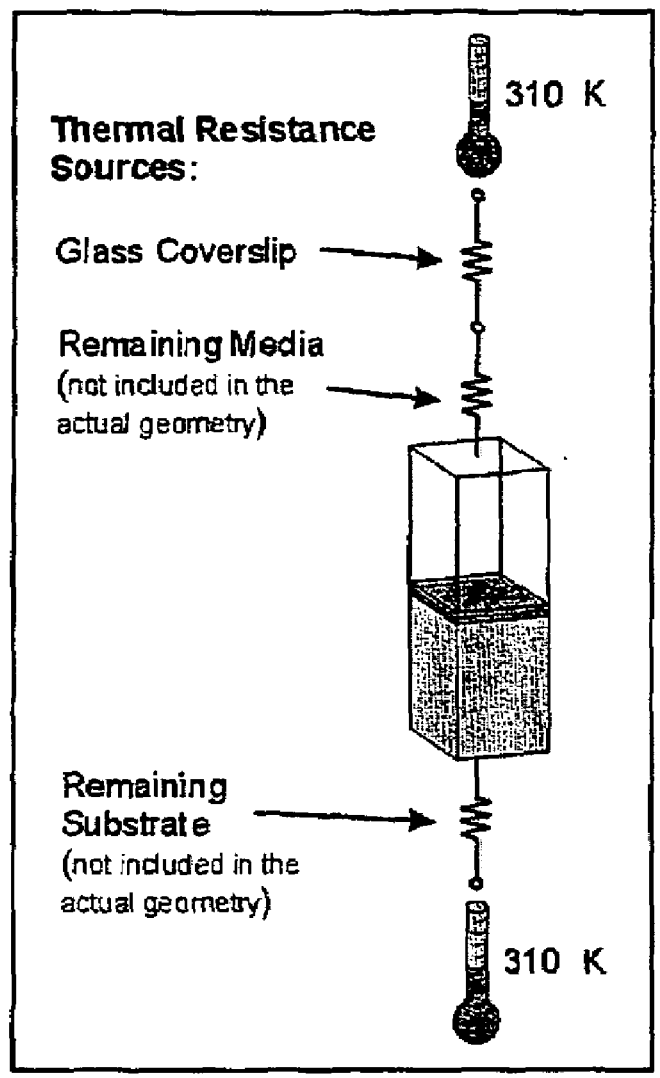
FIG. 15 schematically depicts the approach used to set the heat flux boundary conditions on the top and bottom faces of simulated models. The boundary conditions assume conduction is the primary thermal energy dissipation pathway.

The heights of the substrate and media subdomains were truncated in all geometries evaluated, using boundary conditions that could describe the remaining thermal conduction path to ambient 37° C. temperature regimes, however, they were large enough to permit natural e-field attenuation (FIG. 15). A resistive thermal model, described by Eqn. 5 was then used, to introduce effective heat transfer coefficients for the top and bottom surfaces to the system solver.

$$R_{t,cond} = \sum_i \frac{L_i}{k_i} = \frac{1}{h_{eff}} \qquad \text{[Eqn. -5]}$$

$R_{t,cond}$ indicates the thermal resistance associated with the conductive path. $L_i$ is the distance from the top or bottom boundary to either the next material in the heat flow path or a location where the temperature is set to a specified, known value. $k_i$ is the thermal conductivity of a given material and $h_{eff}$ is the effective heat transfer coefficient.

In the case of the top boundary condition, the heat flow path traveled through a remaining amount of media, through a coverslip, and finally to the set ambient temperature of 37° C. For the bottom boundary condition the heat traveled through a remaining amount of the system substrate and out to the 37° C. temperature ambient. The values for the heat transfer coefficient plugged directly into the heat flow relation of Eqn. 6 and prescribed temperatures for the top and bottom surfaces of the geometry.

$$q_x'' = h_{eff}(T_{s,1} - T_{s,2}) \qquad \text{[Eqn. -6]}$$

In this relation $q_x''$ amounts to the heat flux. $T_{s,2}$ matched the isotherm temperatures that would have been seen at the top and bottom surfaces if the remainder of the media/coverslip and substrate thicknesses had been included in the simulated model. Avoiding a need to mesh materials above and below these top and bottom boundary conditions again reduced the number of equations need for system evaluation. $T_{s,1}$ equalled the external ambient temperature for the system.

Table 2 lists the set of electrical and thermal boundary conditions as well as general material properties used for simulations of some of the embodiments of the device.

Table-1: Material properties and boundary conditions used in some simulations.

Figure 16:
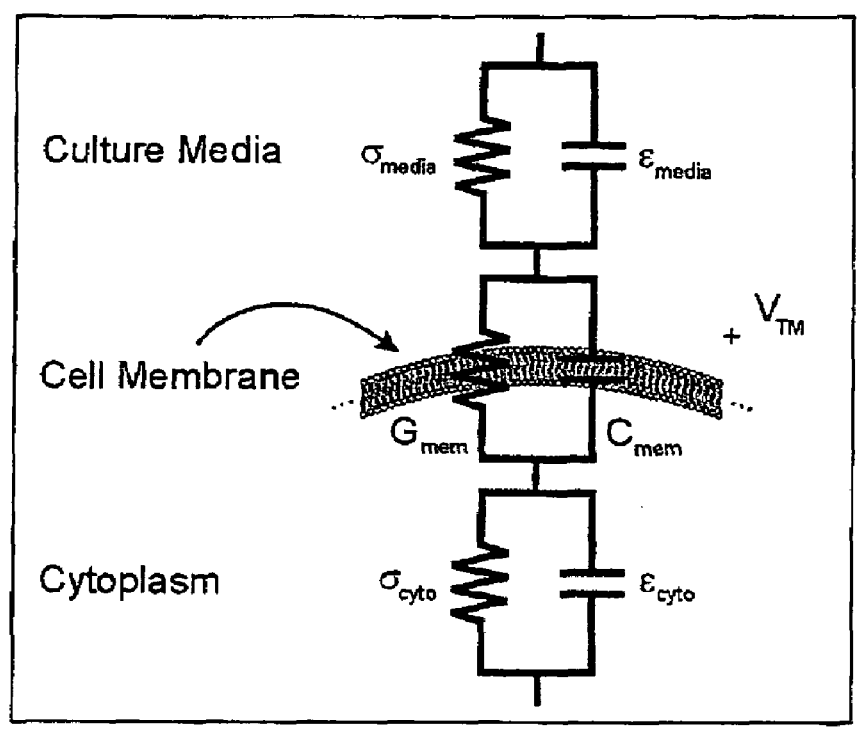
FIG. 16 demonstrates a circuit model reduction characterizing the cell/culture media interface. Depending upon the operating frequency of the DEP drive electrodes, the circuit can be either resistance or capacitance dominated. The transmembrane voltage is the key parameter to monitor for preservation of cell health.

After porting the field data to a Matlab workspace, additional performance characteristics for the traps were assessed. Beyond a given design's ability to hold cells in a specified location, it is important to assess and understand the impact that electroquasistatic fields can have on biological cells. It was important to simulate the sorts of biological effects that could result from exposure of individual mammalian cells to frequencies beneficial to dielectrophoretic manipulations (typically 10's of kHz to 10's of MHz). Producing this sort of information relied upon the use of a previously developed circuit model describing a mammalian cell stationed within a surrounding fluid. FIG. 16 provides an illustration of the RC layout used to describe the conduction pathways from an external source through the media and cell membrane and into the cytoplasm of a cell. As the frequency of the driving signal is varied, the relative effects of the resistive and capacitive elements in the circuit define where specific voltage drops occur in the system.

The cell membrane is an anisotropic reaction interface that serves as a site for interactions between species located on its opposing surfaces. It is generally the dominant mechanism through which the cell interacts with external fields in the DEP frequency range. When subjected to external fields the rates of the reactions taking place at this boundary can be altered. Various models including electroconformational coupling (ECC) and descriptions of an oscillatory activation barrier (OAB) have been used when describing these types of reaction modifications. Usually mammalian cell membranes have higher electrical resistivities than the adjacent media and cytoplasm and as a result tend to experience the bulk of the voltage drop at low frequencies. In this operational regime the circuit model reduces to a set of connected series resistances. The magnitude of that drop is provided in Eqn. 7.

| | Electrical Boundary Conditions | | | Silicon & SU-8 Processes | |
|---|---|---|---|---|---|
| Perimeter Surfaces | Electrical Insulation | $n \cdot J = 0$ | | — | |
| Internal Non-Electrode Surfaces | Electrical Continuity | $n \cdot (J_1 - J_2) = 0$ | | — | |
| Electrodes | Electric Potential | $V = V_0$ | | $V_{M1} = 5$ [V]; $V_{M2} = -5$ [V] | |
| | Thermal Boundary Conditions | | Silicon Process | SU-8 Process | |
| Perimeter Surfaces | Thermal Insulation | $n \cdot (k\nabla T) = 0$ | — | — | |
| Top Geometry Surface | Heat Flux | $n \cdot (k\nabla T) = h(T_{s,1} - T_{s,2})$ | $h = 4303$ [W/m$^2$K]; $T_{s,1} = 310$ [K] | $h = 4303$ [W/m$^2$K]; $T_{s,1} = 310$ [K] | |
| Bottom Geometry Surface | Heat Flux | $n \cdot (k\nabla T) = h(T_{s,1} - T_{s,2})$ | $h = 328889$ [W/m$^2$K]; $T_{s,1} = 310$ [K] | $h = 1189$ [W/m$^2$K]; $T_{s,1} = 310$ [K] | |
| Material | Thermal Conductivity (k) [W/mK] | Density ($\rho$) [kg/m$^3$] | Heat Capacity ($C_p$) [J/kgK] | Complex Conductivity ($\sigma$) | Relative permittivity ($\epsilon_r$) |
| Silicon | 148.0 | 2330 | 712 | $4E-4 + j * 2\pi * 10E-6 * \epsilon_0 * 11.8$ | 11.8 |
| Silicon Dioxide | 1.4 | 2200 | 1000 | $1E-18 + j * 2\pi * 10E-6 * \epsilon_0 * 3.9$ | 3.9 |
| Phosphate Buffered Saline | 6 | 1000 | 4184 | $1 + j * 2\pi * 10E-6 * \epsilon_0 * 80$ (ndep) $1 + j * 2\pi * 10E-6 * \epsilon_0 * 80$ (pdep) | 80 0 |
| SU-8 | .2 | 1220 | 1090 | $1E-18 + j * 2\pi * 10E-6 * \epsilon_0 * 4.0$ | 4.0 |
| Pyrex | 1.2 | 2230 | 726 | $2.5E-5 + j * 2\pi * 10E-6 * \epsilon_0 * 4.6$ | 4.6 |

$$|V_{tm}| = \frac{1.5|E|R}{\sqrt{1 + (\omega\tau)^2}} \qquad [\text{Eqn-7}]$$

where $\omega$ is the angular drive frequency of the signal and $\tau$ is the system time constant expressed as $$\tau = \frac{RC_{mem}\left(\rho_{cyto} + \frac{\rho_{media}}{2}\right)}{1 + RG_{mem}\left(\rho_{cyto} + \frac{\rho_{media}}{2}\right)} \qquad [\text{Eqn.-8}]$$

In this relation $\rho_{cyto}$ and $\rho_{media}$ represent the electrical resistivity of the cytoplasm and cell culture media respectively. While this analytical description, does offer a mechanism for the attenuation of induced transmembrane voltages above the characteristic frequency (1/$\tau$) it fails to fully describe the system response at higher frequencies. For drives in the 100's of MHz the capacitances in the circuit model dominate and the membrane voltage saturates to a constant value.

The high resistance and small thickness of the cell membrane tend to magnify the effects of external fields, at low frequencies. This field amplification is mathematically described through the following simplification:

The field inside of the membrane, $E_{tm}$ is equal to the external field scaled by the 1.5R/$\Delta$($\approx$1000) ratio. Mapping out the transmembrane voltage as a function of frequency thereby offers a mechanism for monitoring the effective load to which the external field subjects the cell. Because the cell membrane sees the brunt of the induced electromagnetic stress and it is a known site for the transduction of various chemical effects, it is important to design traps capable of operating in frequency ranges that induce minimal transmembrane voltages.

Inducing transmembrane voltages of less than 130-150 mV reportedly does not negatively impact cell division rates, cell motility, or cell viability, though even low induced transmembrane voltages result in the upregulation of cfos and the transcription of other unidentified genes. Thus designs wherein the corresponding induced transmembrane voltages fall 100 mV are desirable as presumably resulting in fewer deleterious effects on the entrapped cells.

$$|V_{tm}| = \frac{1.5|E|R}{\sqrt{1 + (\omega\tau)^2}} \approx 1.5|E|R \qquad [\text{Eqn.-9}]$$

$$E_{tm} = \frac{|V_{tm}|}{\Delta} = \left(\frac{1.5R}{\Delta}\right) \cdot E \qquad [\text{Eqn.-10}]$$

Figure 17:
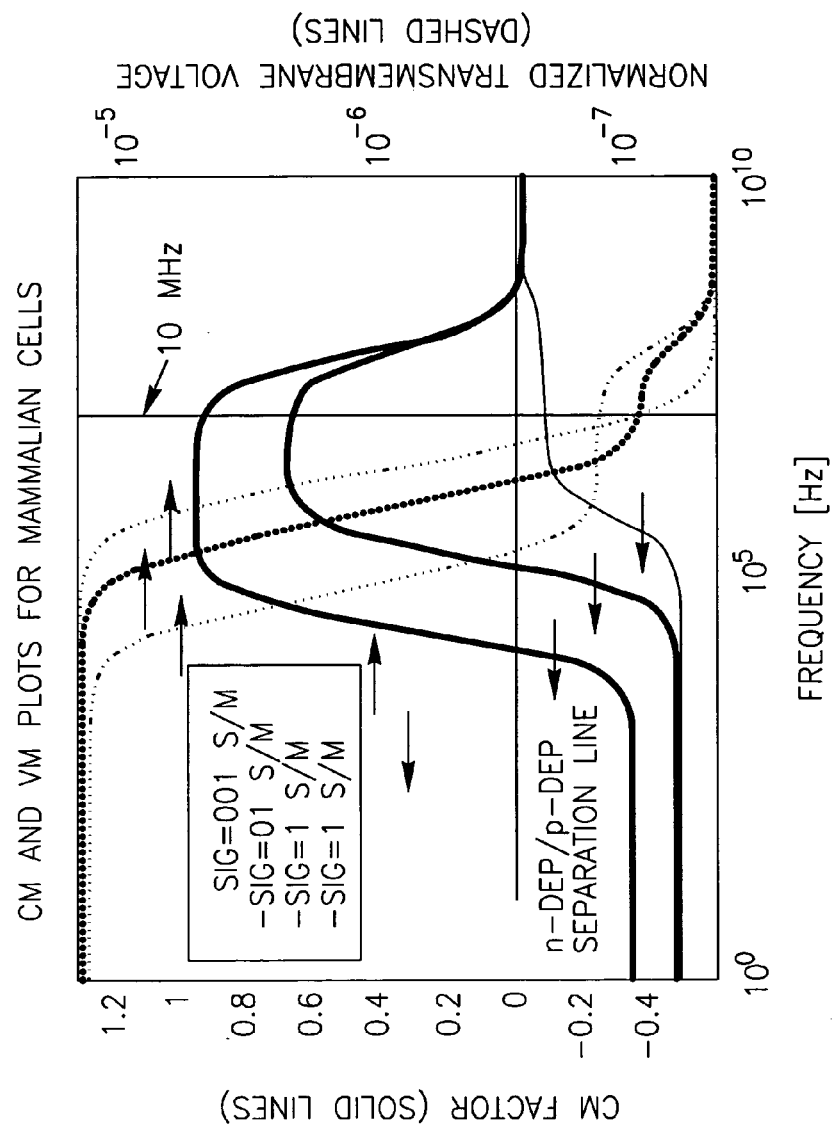
FIG. 17 depicts a DEP operational roadmap for device designs. In general, high frequencies reduce the induced transmembrane voltages. Both the magnitude and sign of the CM factor vary over the examined frequency range. Positive CM factors yield p-DEP trapping while negative CM factors mandate n-DEP effects. The 10 MHz line demarks the frequency chosen for all simulation work.

FIG. 17 is a plot the transmembrane voltage induced by a normalized field of 1V/m as a function of frequency along with overlaying curves to outline the behavior of the real component of the CM factor. Four curves outline the effect that varying conductivities have on the two charted parameters. In general the transmembrane voltages decline with increasing frequency, while the magnitude of the CM factor varies in a non-monotonic fashion and its sign flips throughout the examined range. A 10 MHz line highlights the location of the frequency chosen for described simulations, a value which is well suited for maximizing the amplitude of DEP force, positive or negative, and minimizing transmembrane voltages in trapped cells.

n-DEP Trap Modeling

Figure 18:
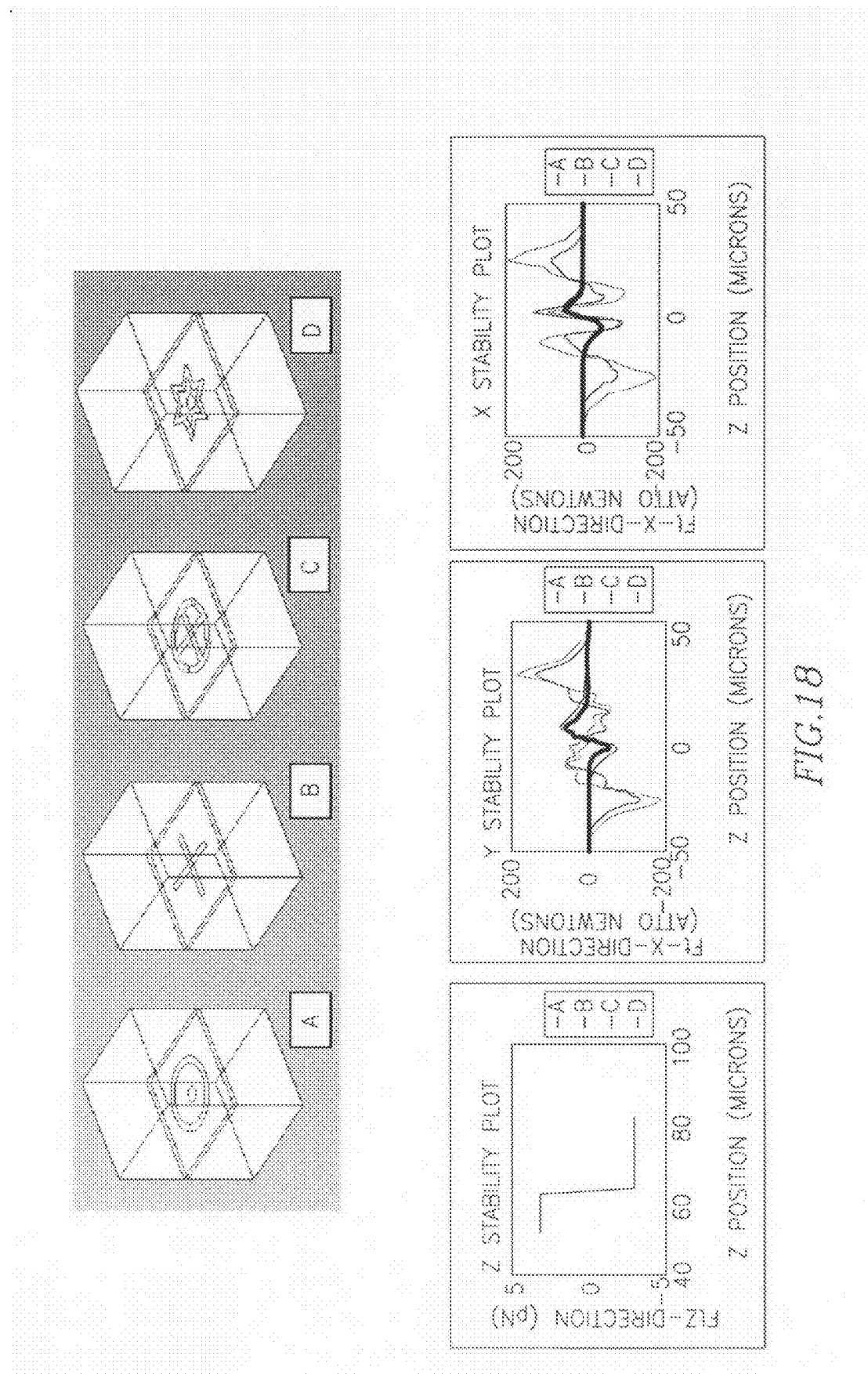
FIG. 18 demonstrates several example geometries examined and tested in pursuit of planar n-DEP trap designs. The corresponding stability plots for the four designs shown indicate that despite some level of stability in the Z-direction. In all of the cases shown in this figure, the geometries were constructed using a silicon substrate; a 3 mm thick silicon dioxide insulating layer with one electrode on its top surface and one electrode imbedded in its center; and a PBS media solution.
Figure 19C:
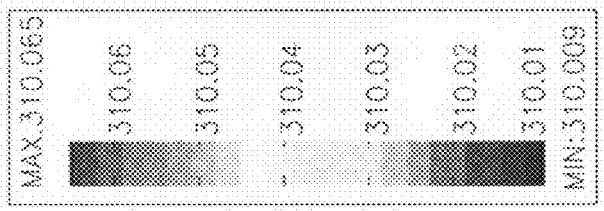
FIG. 19 demonstrates half-model temperature profiles and their associated Z stability curves for the three pit-based designs described. Plan views accompany each of the designs to elucidate their associated electrode configurations. (A) presents a pit flanked by two straight-line electrodes while (B) and (C) show rounded and toothed layouts. The larger field gradients induced using the more complex geometries produce enhancements in trapping characteristics but come at the expense of higher temperature rises above ambient.
Figure 19B:
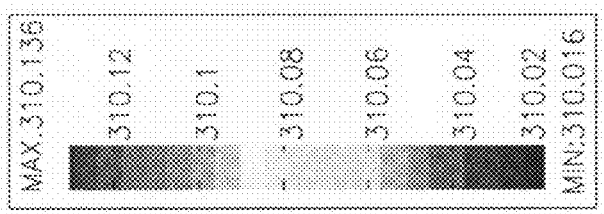
Figure 19A:
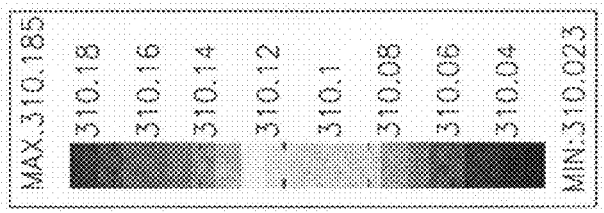
Figure 19D:
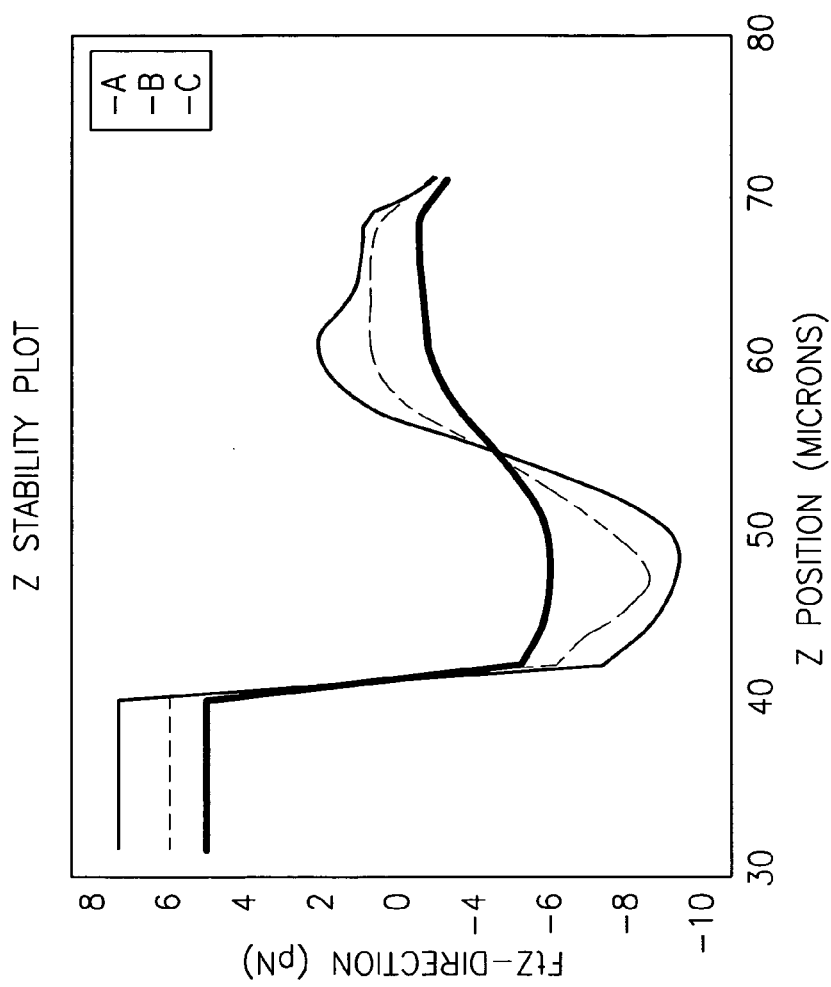

A library of electrode configurations with varied geometries was constructed and evaluated via Femlab and Matlab, as described herein, with geometries such as ring-dot, cross, star, and an assortment of other shapes (FIG. 18). Four test cases shown in the figure indicated that the z-stability plots were essentially identical and demonstrated overlapping curves for z-directed forces (gravity, buoyancy, DEP, normal) that would act on a cell 20 microns in diameter positioned at the center of each design with no fluid flow in the media subdomain. The negative slope of the curves as they pass through the zero value on the ordinate (a general condition for stability in these types of plots) indicates that there is a balance between the normal force from the electrode surface (directed towards the right in this chart) and the gravitational forces and DEP forces pushing downward on the cell (directed towards the left in this chart). The force balance shows that there is a 3 pN force pushing down on cell, which may be substantial enough to hold cells against disrupting fluid flows.

A series of designs with identical electrodes implemented in two test material systems was also modeled. In one, a silicon substrate into which pit formations were carved, and on top of which was placed an insulating oxide layer with various electrode layouts. In another, a pyrex substrate onto which a 20-micron-thick layer of SU-8 photoresist was deposited, was patterned in the shape of a cylindrical well. Electrodes were then designed to sit on top of the SU-8 layer and surround the upper edges of the pit.

FIG. 19 shows three sample half-model designs implemented in the silicon-based material system. In addition to the z-stability plot, planar views of the electrode geometries and images of the corresponding temperature profiles are shown. In the three cases displayed, stable holding characteristics were evident, as indicated by the negative slope of the curves crossing the zero value of the ordinate for all z-positions within the well (the z-position of 31.5 microns marks the bottom of the pit structure while 51.5 microns corresponds to the top of the well) and maximum system temperature rises above ambient were less than two tenths of a degree Celsius for a 1 volt potential difference applied across the electrodes. The gear layout did in fact rendered the strongest z-stability trapping forces, though at the expense of higher maximum temperature rises in the system.

Figure 20C:
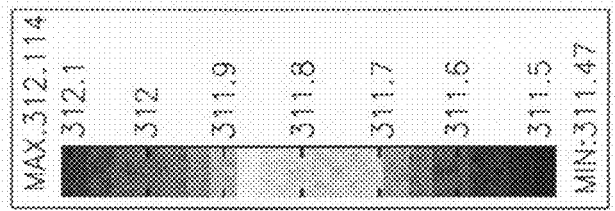
FIG. 20 depicts the same three electrode configurations examined in FIG. 19 implemented using an alternative SU-8 based fabrication process.
Figure 20B:
Figure 20A:
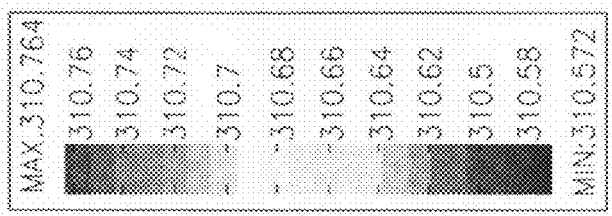

The same electrode structures implemented in the SU-8-based process (see FIG. 18) provided essentially the same z-stability trapping characteristics but for each case the maximum temperature rise above ambient was larger than the corresponding silicon-based designs (FIG. 20). FIG. 21 provides a pictorial view of another embodiment of an n-DEP trap design along with several performance metrics. Maximum system temperature rises were modeled as 0.057° C.; the maximum holding force was mapped to 5 picoNewtons for a 1V applied potential; and the maximum induced transmembrane voltage for the same applied potential was well below the 100 mV limit suggested by others in the art.

p-DEP Trap Modeling

Figure 22:
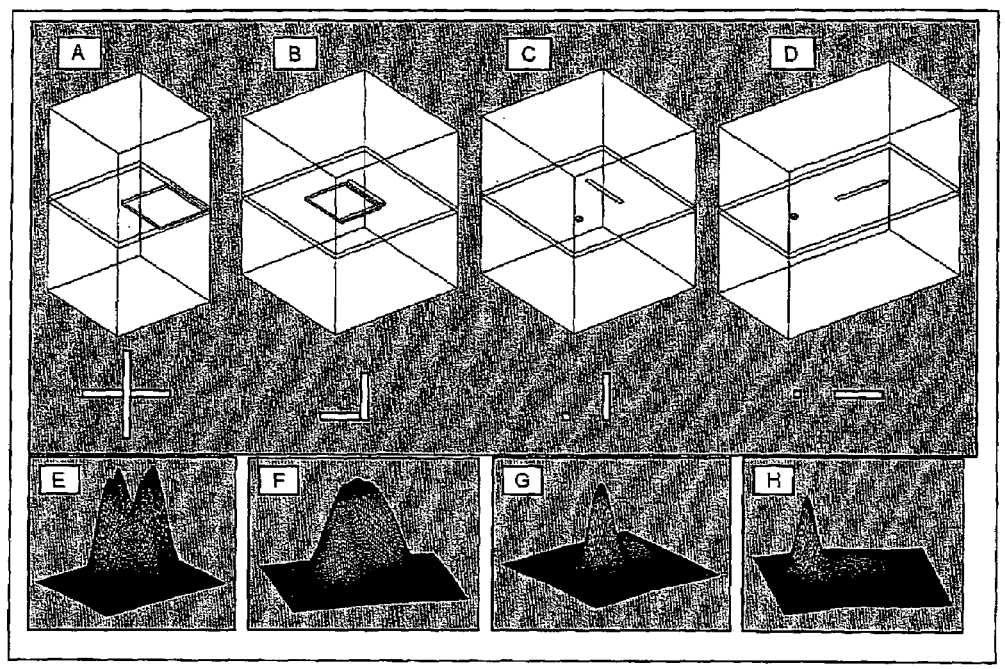
FIG. 22 demonstrates a set of four designs (A-D) for p-DEP trap configurations The corresponding normE2 (where normE= $?(Ex2+Ey2+Ez2)$) plots (E-H) are provided below each design in this sequence. (The normE2 behavior of the traps is directly related to the magnitude and spatial localization of the DEP trapping force.) (A) shows a quarter model of a cross electrode design. This first renders four closely bunched traps (E). A second layout is one fourth of the original cross geometry (B), which rendered a single trap that was dispersed spatially (F). Two line-dot setups were tested (C and D), producing enhanced spatial trapping resolution (G and H). The non-collinear layout (C) rendered a larger peak value in its corresponding normE2 plot.

Multiple geometries were assessed, shown in both pictorial format as well as planar view in FIG. 22. A simple intersecting cross geometry, which due to the presence of the high field region established between the electrodes, produced four spatially separated traps. An L-configuration was also evaluated, which provided a single, though largely dispersed trap site. Two line-dot arrangements were evaluated as well.

Figure 23:
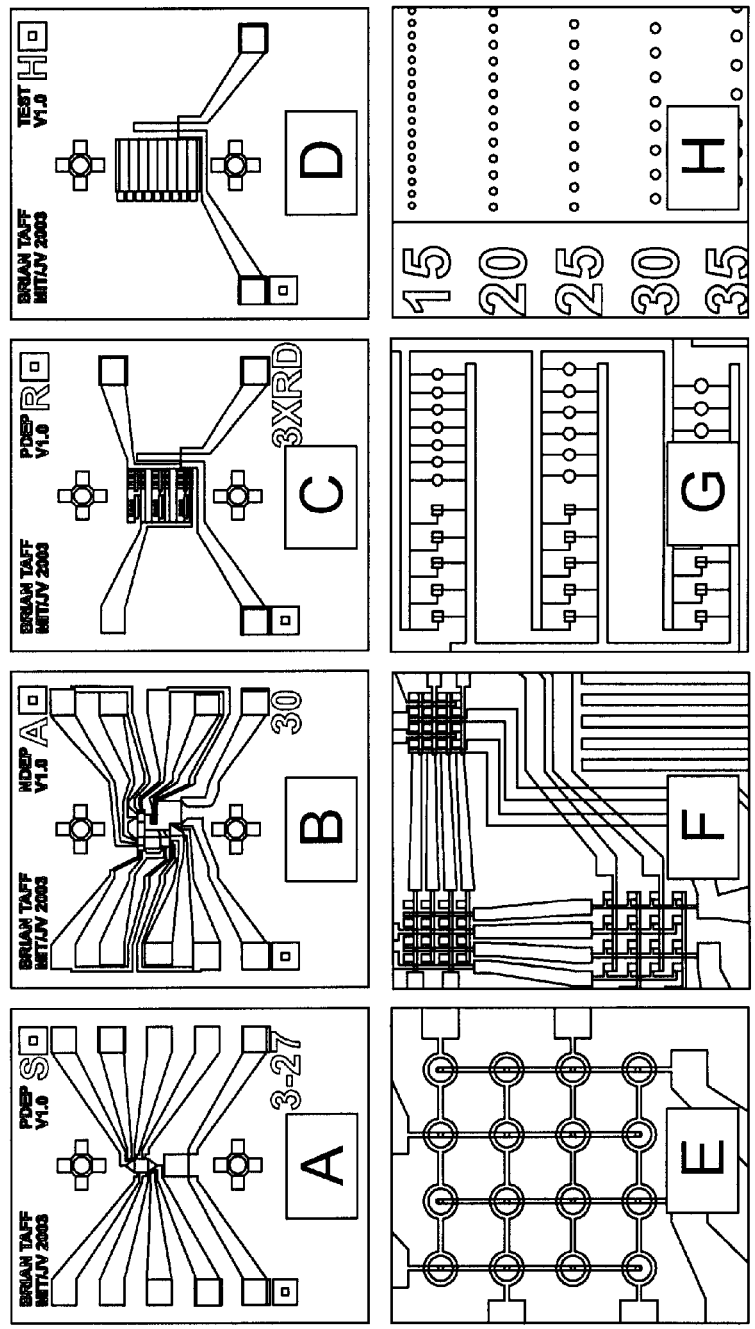
FIG. 23 depicts embodiments of four chip types for use in mask designs. Images (A) and (E) show a layout employing a single 4×4 trap array in full-scale and close-up forms. (B) and (F) present matrix chips which use three separate 4×4 grids for examining the effect of trap spacing on capture potential. Pictures (C) and (G) offer row-chips which are strictly for use as tools to empirically measure trap strength. (D) and (H) outline a specific chip design with an assortment of holes of various diameters, not activated with any electrodes, for use as a platform for measuring cell diameters.

Other geometries evaluated included a series of ring-dot structures. FIG. 23 provides a descriptive layout of the embodied p-DEP design type along with an example of the associated sharply pointed normE$^2$ plots and a planar view of their overhead architectures. In the plan view of (C) two parameters "A" and "B" are outlined. To assess the relative influence of fluctuations of these two dimensions on the trapping performance of a generalized ring-dot geometry, arbitrary dimensions for each were chosen, then paired to form a collection of five distinct trap geometries, which were evaluated via Matlab simulations to assess the z-directed holding characteristics, trap strengths, transmembrane voltages, maximum associated temperature rises and fluid flow rates against which they could hold cells in position. The collection of data generated as a part of this investigation is provided in Table 3.

TABLE 3

Performance characteristics of embodiments of p-DEP traps

| A (μm) | B (μm) | Q (μL/min) | max\|normE\|$^2$ (V$^2$/m$^2$) | Ft-z (pN) | Trap Strength (pN) | V$_{TM}$ (mV) | Max. Temp. Rise (° C.) |
|---|---|---|---|---|---|---|---|
| 3 | 27 | 3.0/3.1 | 1.7406E10 | 103.0965 | 43.3436 | 11.6241 | 0.017 |
| 3 | 20 | 2.7/2.8 | 1.5305E10 | 96.7396 | 39.3091 | 10.8999 | 0.017 |
| 3 | 34 | 2.6/2.7 | 1.5382E10 | 91.9449 | 37.0796 | 10.9273 | 0.016 |
| 2 | 27 | 0.9/1.0 | 9.0663E9 | 33.6884 | 13.8285 | 8.3892 | 0.015 |
| 5 | 27 | 6.1/6.2 | 1.4168E10 | 247.0430 | 86.8339 | 10.4874 | 0.002 |

| A (μm) | B (μm) | Q (μL/min) | V required (V) | max\|normE\| (V/m) | V$_{TM}$ (mV) | Max. Temp. Rise (° C.) |
|---|---|---|---|---|---|---|
| 3 | 27 | 2.7/2.8 | 0.95 | 1.2534E5 | 11.0429 | 0.015 |
| 3 | 20 | 2.7/2.8 | 1.00 | 1.2371E5 | 10.8999 | 0.017 |
| 3 | 34 | 2.7/2.8 | 1.01 | 1.2526E5 | 11.0366 | 0.017 |
| 2 | 27 | 2.7/2.8 | 1.67 | 1.5901E5 | 14.0100 | 0.041 |
| 5 | 27 | 2.7/2.8 | 0.67 | 7.9751E4 | 7.0265 | 0.007 |

Table 3: The top table displays the performance characteristics of five p-DEP trap designs where the applied potential across the electrodes is 1 V. The bottom table shows the same five traps examined when the voltages applied to the electrodes is varied until the hold/release flow rate meets a 2.7/2.8 μL/min value.

The top table lists the model responses for cases where a 1V potential difference is applied across the electrodes. The Q values in this chart are denoted as fractions where the value in the numerator provides the maximum flow rate against which the system can hold a cell in the trap and the denominator is the smallest flow rate needed for dislodging cells from activated electrodes. These flow rate calculations assume that the flow within the media is purely x-directed and amounts to a laminar Poiseuille flow profile through a chamber with a height of 100 μm and a width of 2 mm.

The Ft-z and trap strength values list the peak amplitudes in the z-stability and x-stability curves respectively for a no flow condition. Transmembrane voltages for the given designs are determined in cases where the maximum normE field values in the entirety of the simulated geometries are the driving force for the potential drop.

The lower chart in Table 3 reverses the situation presented in the upper table by specifying a hold/release flow rate for each design and then backing out a corresponding and requisite electrode voltage necessary for matching the prescribed flow rate behavior. Transmembrane voltages are calculated as in the upper chart, and maximum temperature rises are read directly from the output of Femlab temperature simulations. These examinations each normalized in accordance with a distinct parameter helped me to try and distinguish relative differences in the trap behaviors.

The five traps demonstrated similar performance characteristics. When compared to the n-DEP designs these layouts present much larger trapping forces. In general, variations in the "A" parameter produced larger swings in the flow rate and corresponding required electrode voltage behaviors than did modifications in the "B" variable.

Example 6

Chip Fabrication

A 13 mm×13 mm chip footprint was used, which was labeled with macroscopically visible tags to enable quick sorting and ease in positioning the drill holes necessary for fluidic port connections. Resistors with target resistances of 100 Ω were placed on each of the chips to provide an avenue for measuring on chip-temperatures. Alignment patterns in both the upper right and lower left hand corners of each chip were incorporated.

One embodiment of chip architectures is provided in FIG. 23. Layouts of individual 4×4 matrices positioned at the center of the die, or three implementations of the 4×4 grid structures associated with the single "array" chips, layouts comprised of simple rows containing different trap designs, or a series of distinct STS-etched well structures of various diameters are shown in the Figure.

Five separate mask layers were used for constructing each chip design Different patterns for each of the two metal levels, one for the intermetal dielectric, another for the thermal oxide and STS etches, were used and a final mask for the SU-8 dam layout All masks with the exception of the SU-8 layer design (created through a transfer process from an overhead transparency to a photopaternable chrome plate) were purchased from Advanced Reproductions (North Andover, Mass.) and laser etched into chrome coated glass plates.

A single silicon wafer was processed for thermal oxidation, M1 patterning, and the subsequent PECVD oxide deposition (see Table 4).

TABLE 4

Microfabrication Process Flow for 4 × 4 cell trapping array:

1) RCA clean 6" silicon wafers
2) Grow wet thermal oxide - 1.5 microns thick

TABLE 4-continued

Microfabrication Process Flow for 4 × 4 cell trapping array:

3) Sputter on 5000 Å aluminum
4) Spin on standard positive photoresist - 1 micron thick
5) Mask aligner/expose photoresist
6) Photoresist development
7) Descum to remove photoresist from areas where not desired
8) Plasma etch aluminum - use either $Cl_2$ or $BCl_3$ - include dump rinse step
9) Ash to remove remaining photoresist prior to $SiO_2$ deposition
10) PECVD deposition of blanket $SiO_2$ film - 1.5 microns thick
11) Sputter on 5000 Å aluminum
12) Spin on standard positive photoresist - 1 micron thick
13) Mask aligner/expose photoresist
14) Photoresist development
15) Descum to remove photoresist from areas where not desired
16) Plasma etch aluminum - use either $Cl_2$ or $BCl_3$ - include dump rinse step
17) Ash to remove remaining photoresist
18) Spin on standard positive photoresist - 1 micron thick
19) Mask aligner/expose photoresist
20) Photoresist development
21) Descum to remove photoresist from areas where not desired
22) Wet etch of secondary oxide in Transene's Silox Vapox III - timed
23) Ash to remove remaining photoresist
24) Spin on standard positive photoresist - at least 1 micron
25) Mask aligner/expose photoresist
26) Photoresist development
27) Descum to remove photoresist from areas where not desired
28) Wet etch of primary oxide in BOE or Transene's Silox Vapox III
29) Silicon deep trench etch - 20 micron depth etch
30) Ash to remove remaining photoresist
31) Spin on SU-8 photoresist
32) Mask/aligner expose photoresist
33) Solvent wet station for photoresist development
34) Descum to remove photoresist from areas where not desired
35) Coat wafer with OCG 825 photoresist
36) Cut wafer into individual die
37) Wirebond chips to packages A schematic of the fabrication process is provided in FIG. 24. The growth of thermal oxide layers on silicon is a process, which requires increasingly lengthy amounts of time for given linear increases in oxide thickness. This behavior results because new oxide growth is only realized at the oxide/silicon interface. As thermal oxides become thicker and thicker oxygen species in the surrounding heated atmosphere must diffuse over greater distances through the already-grown oxide to the underlying silicon. A wet oxidation process may be used to minimize the required furnace time and reduce the expense of this particular fabrication step, which may be conducted in a Thermco 10K 5C-ThickOx tube over the course of approximately 10 hours to produce thermal oxides with an average thickness of 15220 Å. The oxidized wafers were sputter coated using the Endura (Applied Materials, Santa Clara, Calif.) aluminum deposition recipe set for a 5000 Å target thickness (see Table 5).

TABLE 5

| | Endura 5000 Å Aluminum Deposition | | | |
| --- | --- | --- | --- | --- |
| | Step No. | | | |
| | 1 | 2 | 3 | 4 |
| Step Name | Gas Stabilization | Strike | Deposition | Purge |
| Step End Control | By Time | By Time | By Time | By Time |
| Max. Step Time | 10.0 sec | 3.0 sec | 25.0 sec | 75.0 sec |

TABLE 5-continued

Endura 5000 Å Aluminum Deposition

| | Step No. | | | |
|---|---|---|---|---|
| | 1 | 2 | 3 | 4 |
| Process Positive Pressure Control | None | None | None | None |
| Gate Pressure | Full | Full | Full | Full |
| Process Pressure | 0.00 mTorr | 0.00 mTorr | 0.00 mTorr | 0.00 mTorr |
| Wafer Gas Pressure | 5000 mTorr | 5000 mTorr | 5000 mTorr | 0 mTorr |
| DC Power | 0 W | 750 W | 9000 W | 0 W |
| DC Power Ramp Rate | 0 W/sec | 750 W/sec | 4500 W/sec | 0 W/sec |
| Pressure Servo Gass | AR-1: 45 scc | AR-1: 45 scc | AR-1: 45 scc | AR-1: 0 scc |
| Gas Names and Flows | ARH-1: 14 scc | ARH-1: 14 scc | ARH-1: 14 scc | N/A |

The resulting metal film was very uniform and highly reflective. After coating the wafers with SPR 700-1.2 photoresist (Shipley) using the T1HMDS recipe (outlined in Table 6) on the ICL Coater6 (Semiconductor Systems), the M1 layer was exposed using a 2.5 second exposure on the EV1 (Electronic Visions, Phoenix, Ariz.) and then developed using the standard DEV6 recipe on Coater6.

TABLE 6

| Stage 1 | Stage 2 | Stage 3 | Stage 4 | Stage 5 |
|---|---|---|---|---|
| Coater6 "T1HMDS" Standard Photoresist Coating Recipe | | | | |
| 130° C. 30 sec | 130° C. 60 sec | 95° C. 60 sec | 500 RPM 8 sec | 3000 RPM 30 sec |
| Coater6 "TAFFC" Modified Photoresist Coating Recipe | | | | |
| 130° C. 30 sec | 130° C. 60 sec | 95° C. 60 sec | 500 RPM 8 sec | 700 RPM 30 sec |
| Coater6 "DEV6" Standard Photoresist Development Recipe | | | | |
| 115° C. 60 sec | 130° C. 60 sec | 25° C. 60 sec | 400 RPM 25 sec | 3500 RPM 30 sec |
| Coater6 "TAFFD" Modified Photoresist Development Recipe | | | | |
| 115° C. 60 sec | 130° C. 60 sec | 25° C. 60 sec | 400 RPM 42 sec | 3500 RPM 30 sec |

| Step 1 | Step 2 | Step 3 | Step 4 | Step 5 | Step 6 |
|---|---|---|---|---|---|
| SU-8 2100 Protocol (100 µm target thickness) | | | | | |
| Dehydrate | Coat | Softbake | EV1 Exposure | Post-exposure bake | Develop |
| 15 min @ 95° C. on a | Pour on excessive amounts; Spread speed = 500 RPM (15 sec), Spin speed = 1700 RPM (35 sec) | 4 min @ 65° C., ramp to 95° C. and hold at 95° C. for 20 min | Interval exposure mode; 13 seconds on, 45 sec off, repeat 4 times | 1 min @ 65° C., ramp to 95° C. and hold at 95° C. for 10 minutes | ≈10 min in PM Acetate |

With the wafers thus prepped Rainbow plasma etching was conducted as described in Table 7 for patterning the M1 layer.

| Rainbow Etch Protocol | | | | |
|---|---|---|---|---|
| | Step No. | | | |
| | 1 | 2 | 3 | 4 |
| Pressure | 13 | 13 | 10 | 20 |
| Top Coil | 0 | 375 | 375 | 0 |
| Bottom Coil | 0 | 120 | 120 | 0 |
| Gap | 3 | 3 | 3 | 6 |
| $BCl_3$ | 40 | 40 | 40 | 0 |
| $Cl_2$ | 60 | 60 | 40 | 0 |
| $N_2$ | 10 | 10 | 5 | 0 |
| Ar | 0 | 0 | 0 | 120 |
| He | 10 | 10 | 10 | 0 |
| Time | 10 | 8000 Å/min | 20% over etch 6000 Å/min | 15 |

| AME 5000 Etch Protocol "Oxide Pegasus" Cycled Etch for Thermal $SiO_2$ | | | | |
|---|---|---|---|---|
| Step 1 | Step 2 | Step 3 | Step 4 | Step 5 |
| Stabilization | Descum | Stabilization | Etch | Stabilization |
| 20 sec | 20 sec | 30 sec | 180 sec | 150 sec |
| 200 mTorr | 200 mTorr | 200 mTorr | 200 mTorr | 200 mTorr |
| $O_2$ 10 scc | $O_2$ 10 scc | $CF_4$ 8 scc | $CF_4$ 8 scc | $CF_4$ 8 scc |
| | | $CHF_3$ 6 scc | $CHF_3$ 6 scc | $CHF_3$ 6 scc |
| RF = 0 W | RF = 100 W | RF = 0 W | RF = 350 W | RF = 0 W |
| 50.0 Gauss | 50.0 Gauss | 50.0 Gauss | 50.0 Gauss | 50.0 Gauss |
| | | | Cycle steps 4 and 5 through 10 etch cycles | |

| STS Etch Protocol STS "STSHAL-A" | | |
|---|---|---|
| General | Power | Gases |
| Pressure = 30.0 mTorr | APC Mode = Automatic | $C_4F_8$ = 80 sccm |
| APC Mode = Auto | Platen Generator Power = 10.0 W | $SF_6$ = 40 sccm |
| Base press = 5.0 mTorr | Coil Generator Power = 600 W | |
| Press. Trip = 45.0 mTorr | | |

The etch procedure used, enabled effective patterning of features even as small as 3 μm linewidths. After depositing a 1.5 μm thick oxide using the Concept One PECVD silicon dioxide recipe (Table 6), wafers were again coated with a second level of metal in the Endura sputtering system. The M2 photoresist pattern was accomplished using the same coat, expose, and develop routines on the Coater6 and EV1 machines as was used for the M1 sequence.

To evaluate etch depths, the wafer was also exposed to Silox Vapox III for incremental amounts of time, subjected to spin dry operations and then a series of DeKtak profilometer measurements were conducted to read step-height changes in the exposed regions. When the Dektak step heights stopped changing for scans across the M1 layer, it was assumed that the etch had run to completion.

Figure 25:
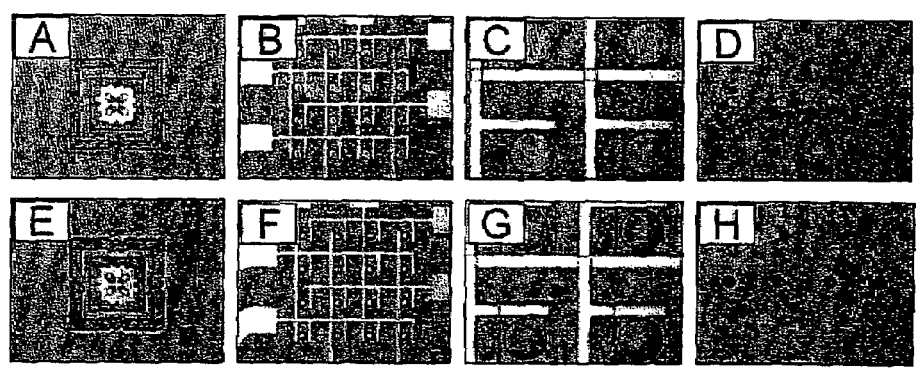
FIG. 25 displays the same features shown in FIG. 24 after a switch to a dry plasma etch process in AME 5000. Minimal undercutting appears. (E)—(H) show again the same images after the STS step. Aside from building the fluid dam and a few subsequent packaging steps, these images present the chips in their final functional form.
Figure 26:
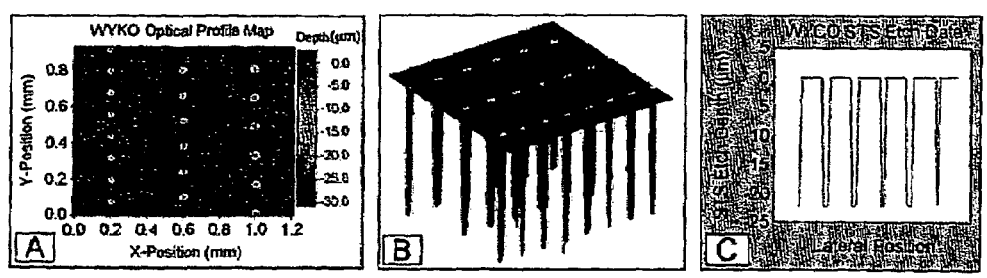
FIG. 26 presents the data used to calibrate the STS etch step in the process. (A) shows a planar view of the optical profile rendered for the final etch depth. Picture (B) is a Matlab graphic of the 3-D data extracted from (A). For ease of depth measurement, a plot along one of the rows of etched holes is shown (C).

The second to last mask layer, served to pattern both the thermal oxide and STS pit layouts in the devices. With one application of a defined photoresist pattern two sequential etches were thus run without the standard intermediary stripping process generally seen. In addition, photoresist coating procedures were conducted by running the TAFFC and TAFFD (See Table 6) programs on Coater6 while boosting EV1 exposure times from 2.5 seconds to 6.5 seconds. This alternative coating routine presented a slower wafer spin speed and produced a thicker photoresist layer (on the order of 2.7 μm). Increasing the photoresist thickness and use of the plasma etch (Table 7), rendered a successful patterning of the thermal oxide layer as shown in the top half of FIG. 25, with successful STS etch shown in the lower half of the figure. The STSHAL-A recipe was used on STS2 to target a 20 μm depth for this step, and pit depths were incrementally measured using the WYKO Optical Profilometer (Veeco, Woodbury, N.Y.), with an outline of the sequence of information obtained for the final etch depth provided in FIG. 26. The measured pit depths are on the order of 22 μm, which ultimately produced actual pit depths of 20 μm once a 2 μm layer of photoresist was stripped from the wafer's top surface.

Figure 27:
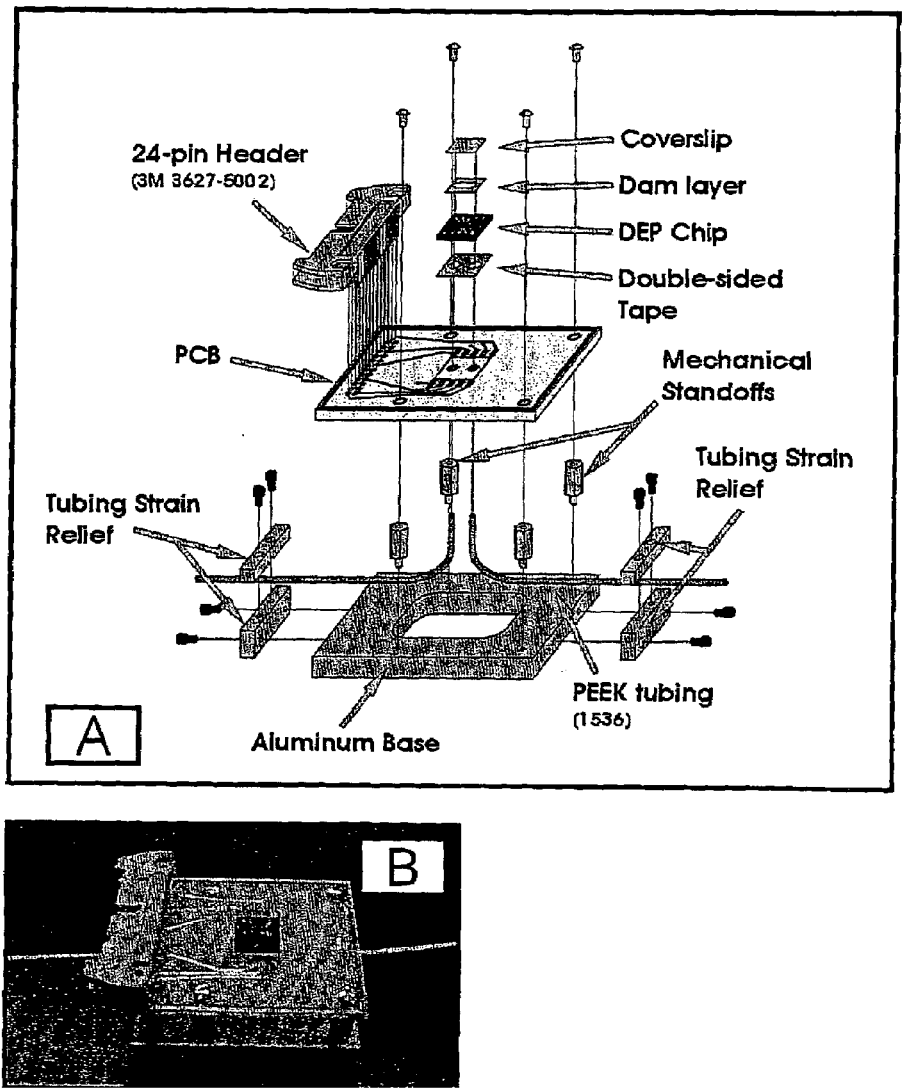
FIG. 27 demonstrates a packaging configuration used for testing DEP chips (A) provides an exploded diagram of all components while (B) shows an assembled model. This setup sits on a microscope stage and readily plugs directly into the external drive circuitry and fluidic control system. The chip-on-board mount avoids the need for a separate specialty chip package.

Individual wafers were coated with thick blankets of OCG 825 positive photoresist (Rohm and Haas, Philadelphia, Pa.) and then baked for half an hour at 90° C. With the protective layer in place, wafers were subjected to a dicing routine using the 2060 blade (cuts streets 220 μm wide) on a DAD-2H/6T diesaw (Disco, Santa Clara, Calif.). Sets of 13 mm×13 mm chips produced were mounted on printed circuit boards, with a general configuration of the chip package shown FIG. 27 in an exploded diagram format along with an actual photograph of an experimental assembly.

Example 7

Addressability of the Device

Figure 28:
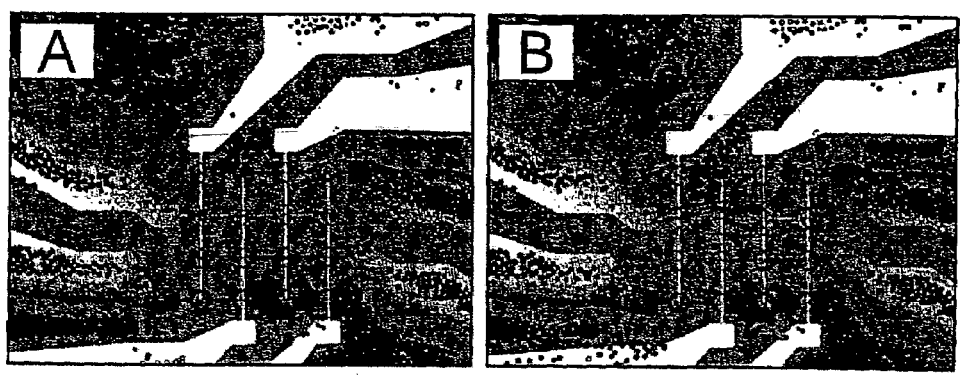
FIG. 28 demonstrates the addressability feature using polystyrene beads on a p-DEP chip. In (A) the red arrow highlights the bead to be released. (B) indicates that beads on the same row escaped with this operation, however two red arrows in (B) show that some beads in the array remained in place.

For p-DEP chip testing of row/column addressability, selective release of individual trapped beads was evaluated using the fabricated device. A plug of 20 μm diameter microspheres were injected into the chamber of the device, all fluid flow was turned off to permit bead settling, followed by activation of the control electrodes. Site specific trapping was seen. A specific trapped bead in the array was selected, and release was attempted by grounding the associated row and column electrodes and initiating a hand-driven fluid flow (FIG. 28). Three individual beads were held in the second row, with the bead located furthest to the right (highlighted with a red arrow in the figure) being successfully dislodged (panel B). Though the other two beads in the row were also freed during this operation, two beads trapped elsewhere in the grid remained trapped and in place, indicating the promise of the device, and highlighted the potential for the addressability scheme.

What is claimed is:

1. A method for adherent cell sorting, comprising:
   i. loading cells in a sorting cytometer, comprising:
      a. a power source;
      b. an array of traps comprising:
         vessels, with dimensions such that each vessel holds a single cell; and
         dielectrically separated crossing electrodes coupled to said power source, surrounding said vessels wherein said electrodes are arranged in a row/column addressing scheme on said array;
      c. an input port coupled to said array; and
      d. an output port coupled to said array, such that individual cells passively enter said vessel; applying a voltage, such that said individual cells are subjected to dielectrophoresis, and are physically trapped within each vessel, under conditions allowing said trapped cells to adhere to said vessels;
   ii. ceasing application of said voltage;
   iii. assaying adherent cells upon cessation of the application of said voltage, such that a population of said adherent cells is identified whose isolation is desired;
   iv. reapplying said voltage to vessels comprising cells whose isolation is not desired, trapping these cells; and
   v. dislodging said cells whose isolation is desired, and collecting said cells from said output port.

2. The method of claim 1, wherein said dielectrophoresis is positive or negative.

3. The method of claim 1, wherein said voltage applied is between 1 and 15 V.

4. The method of claim 1, wherein said cytometer is maintained under controlled temperature, pH, $CO_2$ or Oxygen conditions, or a combination thereof.

5. The method of claim 1, wherein said array is comprised of a transparent material.

6. The method of claim 5, wherein said transparent material is pyrex, quartz or SU-8.

7. The method of claim 1, wherein said array is comprised of silicon.

8. The method of claim 1, wherein said array is coated with a low-autofluorescent material.

9. The method of claim 1, wherein said array, with the exception of said vessels, is coated with a microstamping material.

10. The method of claim 9, wherein said microstamping material is polyethylene glycol or octadecyl-trichlorosilane.

11. The method of claim 1, wherein said vessels are coated with a positively charged material.

12. The method of claim 1, wherein said vessels are coated with at least one protein.

13. The method of claim 12, wherein said at least one protein is an extracellular matrix protein.

14. The method of claim 1, wherein said cells are subjected to an average field strength of between $10^4$ to $10^6$ V/m.

15. The method of claim 1, wherein said cells whose isolation is not desired, said cells whose isolation is desired, or a combination thereof comprise a vector.

16. The method of claim 15, wherein said vector comprises a reporter.

17. The method of claim 16, wherein said reporter is fluorescent.

18. The method of claim 1, wherein assaying said cells produces at least 2 distinguishable cell populations.

19. The method of claim 1, wherein said population of adherent cells is identified by fluorescence microscopy.

20. The method of claim 1, wherein dislodging said cells is effected by the introduction of a solution in said input port.

21. The method of claim 20, wherein said solution comprises trypsin, elastase, papain, a high salt concentration or a chelating agent, or a combination thereof.

22. The method of claim 1, used for the identification of a diseased cell.

23. A sorting cytometer for eukaroytic and/or prokaryotic cells comprising:
   a. a power source for applying voltage;
   b. an array of traps comprising:
      vessels, with dimensions such that each vessel holds a single cell, and wherein said vessels are coated with a positively charged material or said vessels are coated with at least one protein; and
      dielectrically separated crossing electrodes coupled to said power source, surrounding said vessels wherein said electrodes are arranged in a row/column addressing scheme on said array;
   c. an input port, which facilitates flow across said array coupled to said array; and
   d. an output port coupled to said array.

24. The sorting cytometer of claim 23, wherein said at least one protein is an extracellular matrix protein.

* * * * *